United States Patent [19]
Holmes et al.

[11] Patent Number: 5,955,343
[45] Date of Patent: Sep. 21, 1999

[54] STABLE MACROSCOPIC MEMBRANES FORMED BY SELF-ASSEMBLY OF AMPHIPHILIC PEPTIDES AND USES THEREFOR

[75] Inventors: Todd Holmes, Somerville; Shuguang Zhang; Alexander Rich, both of Cambridge; C. Michael DiPersio, Norton; Curtis Lockshin, Lexington, all of Mass.

[73] Assignee: Massachusetts Institute of Technology, Cambridge, Mass.

[21] Appl. No.: 08/293,284

[22] Filed: Aug. 22, 1994

Related U.S. Application Data

[63] Continuation-in-part of application No. 07/973,326, Dec. 28, 1992, abandoned.
[51] Int. Cl.$^6$ ...................................................... C12N 5/02
[52] U.S. Cl. ................................... 435/240.1; 435/240.2; 435/240.23; 435/240.241
[58] Field of Search ............................. 435/240.1, 240.2, 435/240.23, 240.241

[56] References Cited

U.S. PATENT DOCUMENTS 5,122,470 6/1992 Banes ................................ 435/240.241

OTHER PUBLICATIONS

Zhang et al., "Zuotin, a putative Z–DNA binding protein in *Saccharomyces cerevisiae*", *The EMBO J.* 11(10):3787–3796 (1992).

Osterman, D.G. and Kaiser, E.T., "Design and Characterization of Peptides with Amphiphilic β–Strand Structures", *J. Cell. Biochem.* 29:57–72 (1985).

Brack, A. and Orgel, L.E., "β structures of alternating polypeptides and their possible prebiotic significance", *Nature* 256:383–387 (1975).

Brack, A. and Caille, A., Synthesis and β–Conformation of Copolypeptides with Alternating Hydrophilic and Hydrophobic Residues:, *Int. J. Peptide Protein Res.* 11:128–139 (1978).

Brack, A. and Barbier, B., "Early Peptidic Enzymes", *Adv. Spac. Res.* 9(6) : (6)83–(6)87 (1989).

Marqusee S. and Baldwin, R.L., "Helix stabilization by Glu$^-$ . . . Lys$^+$ salt bridges in short peptides of de novo design", *Proc. Natl. Acad. Sci. USA* 84:8898–8902 (1987).

Marqusee, S., et al., "Unusually stable helix formation in short alanine–based peptides", *Proc. Natl. Acad. Sci. USA* 86:5286–5290 (1989).

(List continued on next page.)

*Primary Examiner*—Charles L. Patterson, Jr.
*Assistant Examiner*—Eric Grimes
*Attorney, Agent, or Firm*—Hamilton, Brook, Smith & Reynolds, P.C.

[57] ABSTRACT

Described herein is the self-assembly of amphiphilic peptides, i.e., peptides with alternating hydrophobic and hydrophilic residues, into macroscopic membranes. The membrane-forming peptides are greater than 12 amino acids in length, and preferably at least 16 amino acids, are complementary and are structurally compatible. Specifically, two peptides, $(AEAEAKAK)_2$ $(ARARADAD)_2$, were shown to self-assemble into macroscopic membranes. Conditions under which the peptides self-assemble into macroscopic membranes and methods for producing the membranes are also described. The macroscopic membranes have several interesting properties: they are stable in aqueous solution, serum, and ethanol, are highly resistant to heat, alkaline and acidic pH, chemical denaturants, and proteolytic digestion, and are non-cytotoxic. The membranes are potentially useful in biomaterial applications such as slow-diffusion drug delivery systems, artificial skin, and separation matrices, and as experimental models for Alzheimer's disease and scrapie infection. The sequence of the peptide, EAK16, was derived from a putative Z-DNA binding protein from yeast, called zuotin. The cloning and characterization of the ZUO1 gene are also described.

4 Claims, 14 Drawing Sheets

OTHER PUBLICATIONS

Padmanabhan, S., et al., "Relative helix–forming tendencies of nonpolar amino acids", *Nature* 344: 268–270 (1991).

Seipke, G., et al., "Synthesis and Properties of Alternating Poly(Lys–Phe) and Comparison with the Random Copolymer Poly(Lys$^{51}$, Phe$^{49}$)", *Biopolymers* 13:1621–1633 (1974).

St. Pierre, S., et al., "Conformational Studies of Sequential Polypeptides Containing Lysine and Tyrosine", *Biopolymers* 17:1837–1848 (1978).

Peggion, E., et al., "Conformational Studies on Polypeptides. The Effect of Sodium Perchlorate on the Conformation of Poly–L–lysine and of Random Copolymers of L–Lysine and L–Phenylalanine in Aqueous Solution", *Biopolymers* 11:633–643 (1972).

Trudelle, Y., "Conformational study of the sequential (Tyr–Glu)$_n$ copolymer in aqueous solution", *Polymer* 16:9–15 (1975).

Rippon, W.B., et al., "Spectroscopic Characterization of Poly(Glu–Ala)", *J. Mol. Biol.* 75:369–375 (1973).

Gay, N.J., et al., "A leucine–rich repeat peptide derived from the Drosophila Toll receptor forms extended filaments with a β–sheet structure", *FEBS* 291:87–91 (1991).

Hilbich, C., et al., "Aggregation and Secondary Structure of Synthetic Amyloid βA4 Peptides of Alzheimer's Disease", *J. Mol. Biol.* 218:149–163 (1991).

Halverson, K., "Molecular Determinants of Amyloid Deposition in Alzheimer's Disease: Conformational Studies of Synthetic β–Protein Fragments", *Biochemistry* 29:2639–2644 (1990).

Gasset, M., et al., "Pertubation of the secondary structure of the scrapie prion protein under conditions that alter infectivity", *Proc. Natl. Acad. Sci. USA* 90:1–5 (1993).

Lizardi, P.M., "Genetic Polymorphism of Silk Fibroin Studied by Two–Dimensional Translation Pause Fingerprints", *Cell* 18:581–589 (1979).

Thomas, E.L., "Gigamolecules in Flatland", *Science* 259:43–45 (1993).

Stupp, S.I., "Synthesis of Two–Dimensional Polymers", *Science* 259:59–63 (1993).

Gulik–Krzywicki, T., et al., "Electron microscopic study of supramolecular liquid crystalline polymers formed by molecular recognition–directed self–assembly from complementary chiral components", *Proc. Natl. Acad. Sci. USA* 90: 163–167 (1993).

Smith, Garnet G. and Peck, Garnet E., "Continuous–Flow System for Determination of Diffusion Coefficients: Use of a Natural Membrane," *J. of Pharmaceutical Sciences* 65(5):727–732 (1976).

*Physicians' Desk Reference,* 47th Edition, Medical Economics Data, Montvale, NJ, p. 2598 (1993).

Peppas, Nicholas A. and Langer, Robert, "New Challenges in Biomaterials," *Science* 263:1715–1720 (1994).

Lehn, Jean–Marie, "Self–assembly of double helical, triple helical and deoxyribonucleo–helicate architectures," *Chemistry & Biology,* Introductory issue, xviii–xix (1994).

Fréchet, Jean M., "Functional Polymers and Dendrimers: Reactivity, Molecular Architecture, and Interfacial Energy," *Science* 263:1710–1719 (1994).

Clery, Daniel, "After Years in the Dark, Electric Plastic Finally Shines," *Science* 263:1700–1703 (1994).

Hynes, Richard O., "Integrins: Versatility, Modulation, and Signaling in Cell Adhesion," *Cell* 69:11–25 (1992).

Yamada, Kenneth M., "Adhesive Recognition Sequences," *J. of Biological Chemistry* 266 (20):12809–12812 (1991).

Prieto, Anne L. et al., "Multiple integrins mediate cell attachment to cytotactin/tenascin", *Proc. Natl. Acad. Sci. USA* 90:10154–10158 (1993).

Cima, Linda G. and Langer, Robert, "Engineering Human Tissue", *Chemical Engineering Progress* 89(6): 46–54 (1993).

Barrera, Denise et al. "Synthesis and RGD Peptide Modification of a New Biodegradable Copolyner: Poly(lactic acid–co–lysine)," *J. Am. Chem. Soc.* 115:11010–11011 (1993).

Den Dunnen, W. F. A. et al., "A new PLLA/PCL copolymer for nerve regeneration", *J. of Materials Science: Materials in Medicine* 4:521–525 (1993).

Lin, Horng–Ban et al. "Synthesis, surface, and cell–adhesion properties of polyurethanes containing covalently grafted RGD–peptides," *J. of Biomedical Materials Research* 28:329–342 (1994).

Dagani, Ron, "Biodegradable copolymer eyed as tissue matrix," *C&EN* p. 5 (1993).

WPI Accession No. 92–313679/38 (JP 4–221395) (1992).

WPI Accession No. 92–313678/38 (JP–4–221394) (1992).

```
MFSLPTLTSD ITVEVNSSAT KTPFVRRPVE PVGKFFFLQHA QRTLRNHTWS EFERIEAEKN    60
 -    -  -        ++  -   +         +       + -   -+
          ✪                        ●

VKTVDESNVD PDELLFDTEL ADEDLLTHDA RDWKTADLYA AMGLSKLRFR ATESQIIKAH   120
 +  -   -   -    -     - -   -   +         +  +  +    +   -
 ○

RKQVVKYHPD KQSAAGGSLD QDGFFKIIQK AFETLTDSNK RAQYDSCDFV ADVPPPKKGT   180
++ +  + -  +          -    -      -  -  -      -  -     ++  ++
   ☆                             ●                           ▶○

DYDFYEAWGP VFEAEARFSK KTPIPSLGNK DSSKKEVEQF YAFWHRFDSW RTFEFLDEDV   240
- - - +      -  + -    +   -    ++ -   -       +  -   + -  -
  ●○                  ●                   ☆
                      ●

PDDSSNRDHK RYIERKNKAA RDKKKTADNA RLVKLVERAV SEDPRIKMFK EEEKKEKERR   300
 -  - + -  + -+++ +   +++  -    + +  -  +   -+  + +   -- +++-++
                                                    ▶

KWEREAGARA EAEAKAKAEA EAKAKAESEA KANASAKADK KKAKEAAKAA KKKNKRAIRN   360
 + +  + +   +   + +   +   -  +   +  +  -+  ++ +  + +  +++ + + +
 +●                                         ⁓⁓⁓⁓⁓⁓⁓⁓⁓  ⁓⁓⁓⁓⁓⁓⁓⁓⁓
 ○

SAKEADYFGD ADKATTIDEQ VGLIVDSLND EELVSTADKI KANAAGAKEV LKESAKTIVD   420
 + -  + -   -+ -   +  +    -  -  - +  - +   +  + + +  + -   + -
          ○○                                        ●

SGKLPSSLLS YFV
 +
●

K-D: ionized pair interaction
   distance = 5 + 3 = 8

Q-Q: hydrogen bonding
   distance = 4 + 4 = 8

Peptide A        N-VRVRVDVDVRVRVDVD-c
Peptide B                c-KAKADADAKAKADADA-n

R (6) + D (3) = 9
D (3) + K (5) = 8

Peptide A        N-VRVRVDVDVRVRVDVD-c
Peptide A                c-DVDVRVRVDVDVRVRV-n Peptide B        N-ADADAKAKADADAKAK-c
Peptide B                c-KAKADADAKAKADADA-n

FIG.7C

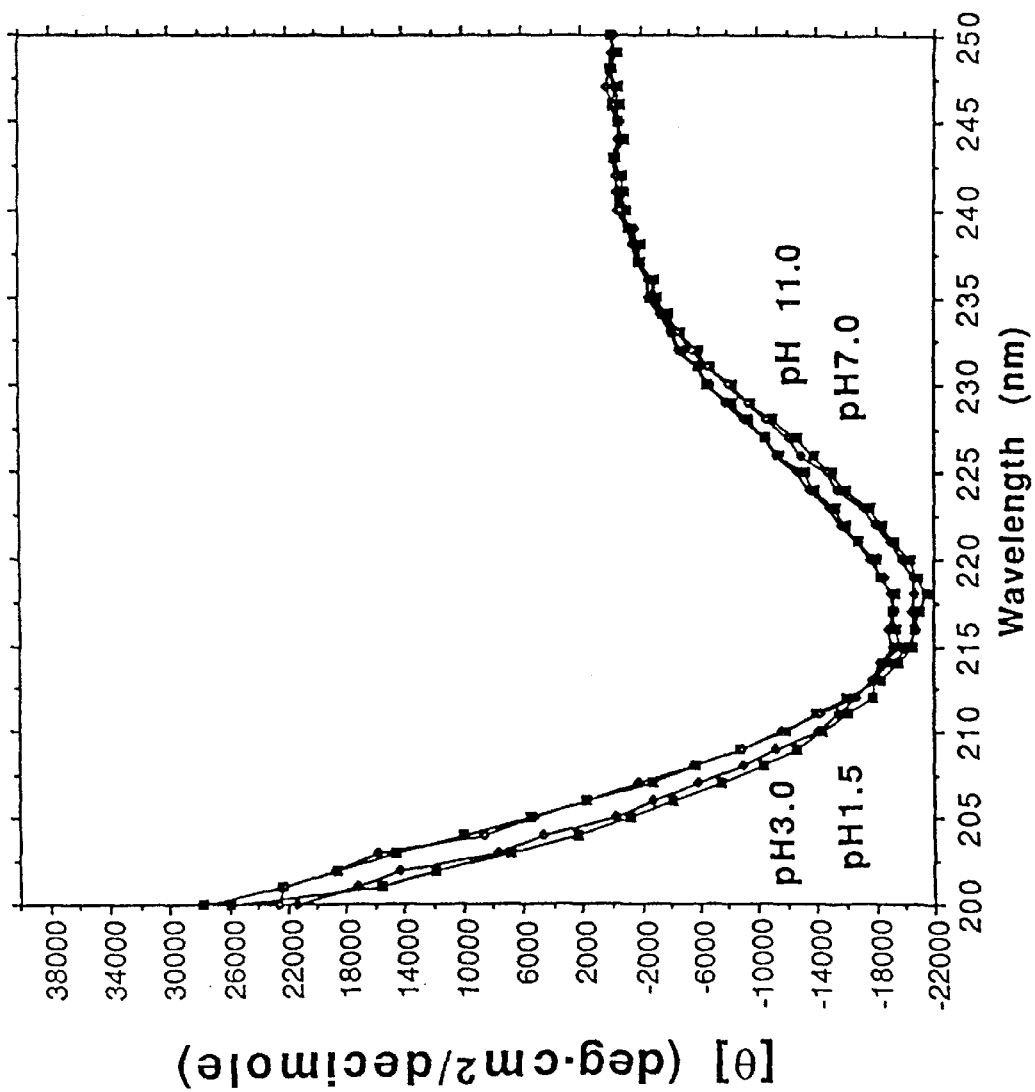

STABLE MACROSCOPIC MEMBRANES FORMED BY SELF-ASSEMBLY OF AMPHIPHILIC PEPTIDES AND USES THEREFOR

RELATED APPLICATION

This application is a Continuation-in-Part of U.S. Ser. No. 07/973,326, filed Dec. 28, 1992, now abandoned, which is incorporated herein by reference.

GOVERNMENT FUNDING

This work was supported by Grant No. NIH-5R37-CA04186 from the National Institutes of Health and by Grant No. N00014-90-J-4075 from the Office of Naval Research. The U.S. Government has certain rights in this invention.

BACKGROUND

Macroscopic membranes play an important role in many biological processes at both the cellular and organismic level. In addition, membranes are used in a number of medical, research, and industrial applications. Physiologically compatible membranes would be especially valuable for biomedical products. At present, the self-assembly of peptides into macroscopic membranes has not been reported.

SUMMARY OF THE INVENTION

The invention relates to the discovery that a new class of biomaterials derived from peptides related to the yeast DNA binding protein zuotin. The oligopeptides are generally stable in aqueous solutions and self-assemble into large, extremely stable macroscopic structures or matrices when exposed to physiological levels of salt. The biomaterials are visible to the naked eye when stained with a dye, Congo Red, and can form sheet-like or fibril structures which have high tensile strength. These materials are substantially resistant to change in pH, heat, and enzymatic proteolysis. The biomaterials can have a fibrous microstructure with small pores as revealed by electron microscopy.

A small peptide termed EAK16 (AEAEAKAKAEAEAKAK, aa 310–325 of SEQ ID NO: 2) was discovered serendipitously to self-assemble into stable macroscopic membranes and filaments in the presence of millimolar concentrations of salt. This invention relates to the self-assembly of peptides into stable macroscopic membranes and filaments. Peptides which form membranes are characterized as being amphiphilic, e.g., having alternating hydrophobic and hydrophilic amino acid residues; greater than 12 amino acids, and preferably at least 16 amino acids; complementary and structurally compatible. Complementary refers to the ability of the peptides to interact through ionized pairs and/or hydrogen bonds which form between their hydrophilic side-chains, and structurally compatible refers to the ability of complementary peptides to maintain a constant distance between their peptide backbones. Peptides having these properties participate in intermolecular interactions which result in the formation and stabilization of β-sheets at the secondary structure level and interwoven filaments at the tertiary structure level.

Both homogeneous and heterogeneous mixtures of peptides characterized by the above-mentioned properties can form stable macroscopic membranes and filaments. Peptides which are self-complementary and self-compatible can form membranes in a homogeneous mixture. Heterogeneous peptides, including those which cannot form membranes in homogeneous solutions, which are complementary and/or structurally compatible with each other can also self-assemble into macroscopic membranes and filaments.

Peptides which can self-assemble into macroscopic membranes and filaments, the conditions under which membrane and filament formation occurs, and methods for producing the membranes and filaments are described and included in this invention.

Macroscopic membranes and filaments formed of the peptide EAK16 have been found to be stable in aqueous solution, in serum, and in ethanol and are highly resistant to degradation by heat, alkaline and acidic pH (i.e., stable at pH 1.5–11), chemical denaturants (e.g., guanidine-HCl, urea and sodium dodecyl sulfate), and proteases in vitro (e.g., trypsin, α-chymotrypsin, papain, protease K, and pronase). The membranes and filaments have also been found to be non-cytotoxic. The membranes are thin, transparent and resemble high density felt under high magnification. Being composed primarily of protein, the membranes and filaments can be digested and metabolized in animals and people. They have a simple composition, are permeable, and are easy and relatively inexpensive to produce in large quantities. The membranes and filaments can also be produced and stored in a sterile condition. Thus, the macroscopic membranes and filaments provided by this invention are potentially useful as biomaterial for medical products, as vehicles for slow-diffusion drug delivery, as separation matrices, for supporting in vitro cell attachment and growth, for supporting artificial tissue, e.g., for in vivo use, and for other uses requiring permeable and water-insoluble material.

Furthermore, the salt-induced assembly of the peptides into insoluble and protease-resistant protein filaments with a β-sheet secondary structure is similar in some respects to the formation of the neurofibrillary filaments and amyloid plaques associated with Alzheimer's disease and the formation of scrapie prion protein filaments liver cirrhosis, kidney amyloidosis, and other protein confirmational diseases. The formation of the macroscopic membranes and filaments can, therefore, be useful as a model system, e.g. to study these pathological processes. For example, such a model system can be used to identify drugs which inhibit filament formation and are thus useful for treating Alzheimer's disease and scrapie infection.

Peptide EAK16 was derived from a region of a yeast protein, zuotin, which exhibits a high affinity for DNA in the left-handed Z conformation. Zuotin was identified by a gel shift assay for Z-DNA binding proteins developed by the Applicants. Applicants further cloned and sequenced the gene encoding zuotin. Characterization of zuotin revealed that the protein is a potential substrate for several protein kinases and identified a putative DNA-binding domain. This invention also includes all or biologically active portions of the zuotin protein and DNA encoding zuotin.

BRIEF DESCRIPTION OF THE DRAWINGS

FIG. 1 shows the amino acid sequence of zuotin (SEQ ID NO: 2) and a number of features of this protein.

FIG. 7A illustrates the self-complementarity and self-compatibility of a peptide (SEQ ID NO: 19).

FIG. 7B illustrates staggering of interacting peptides.

FIG. 7C illustrates peptide interactions in a heterogeneous mixture (SEQ ID NO: 20 and 21).

FIG. 10 shows the stability of the β-sheet structure of EAK16 at different pH.

DETAILED DESCRIPTION OF THE INVENTION

This invention is based on the serendipitous discovery that a small synthetic peptide, EAK16 (AEAEAKAKAEAEAKAK; 310–325 of SEQ ID NO: 2), self-assembles into macroscopic membranes and filaments in an aqueous solution containing a small amount of salt. The sequence of EAK16 was originally found in a region of alternating hydrophobic and hydrophilic residues in a yeast protein called zuotin (heavily underlined in FIG. 1). Initial study of EAK16 revealed that it has a β-sheet secondary structure having unusual stability under various conditions. The structure of the EAK16 and its unusual stability resembles that of β-amyloid protein. When EAK16 was added to the medium of cultured nerve cells in order to test for toxicity, the formation of macroscopic membranes was unexpectedly observed. Observation of a β-sheet structure was surprising, since the sequence of EAK16 was predicted to form an α-helix (Chou and Fasman, 1978). Described below are the structure and properties of the membranes and filaments; peptides which are able to self-assemble into membranes and filaments; methods and conditions for producing the membranes and filaments; the ZUO1 gene and encoded zuotin, from which the EAK16 peptide sequence was derived; and uses of the macroscopic membranes and filaments.

Structure of the Macroscopic Membranes

The EAK16 peptide was observed to form a membranous structure with the appearance of a piece of transparent, thin (about 10–20 μm) plastic membrane when viewed under 100× magnification by phase-contrast microscopy. The membrane was formed in phosphate-buffered saline (PBS) and is colorless and isobuoyant.

The structure could also be observed with the naked eye by staining it bright red with Congo Red, a dye which preferentially stains β-sheet structures and is commonly used to visualize abnormal protein deposition in tissues (Pears, 1960).

At low magnifications (50–100×), the structure looks like a flat membrane. At high magnifications (30,000×) under a scanning electron microscope (SEM), structural details are revealed (FIGS. 3A–H). The membranes in FIG. 3 were formed by adding EAK16 to PBS and prepared for SEM by incubating in 5% glutaraldehyde at 4° C. for 30 minutes, then dehydrated with ethanol and liquid $CO_2$. The photographs were taken at magnifications of 400, 800, 1600, 3000, 6000, 10000, 20000, and 30000× (FIGS. 3A–H).

SEM revealed that the membrane is made up of individual filaments that are interwoven. The architecture of the structure appears to resemble high density felt or cloth. The diameter of the filaments are approximately 10–20 nm and the distance between the fibers are approximately 50–80 nm.

Figure 4:
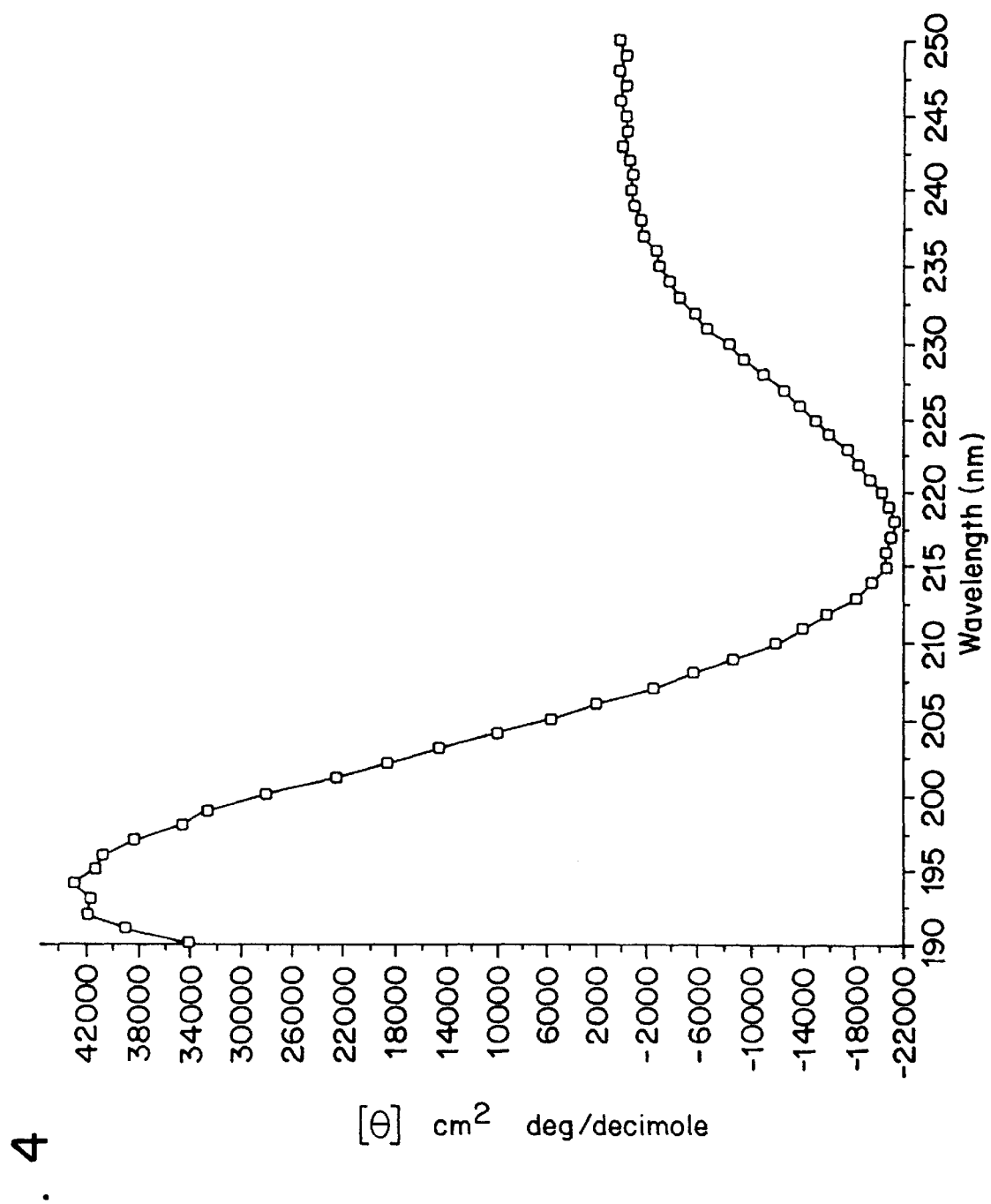
FIG. 4 is the typical β-sheet circular dichroism spectrum of the EAK16 peptide.

The β-sheet secondary structure of the membranes was confirmed by circular dichroism (CD) spectroscopy (FIG. 4). The EAK16 peptide was dissolved in water (10 μM) and the CD spectrum was taken. A typical β-sheet CD spectrum with an absorbance minimum at 218 nm and a maximum at 195 nm was detected. The β-sheet secondary structure of EAK16 was surprising, since a number of short peptides containing alanine, glutamic acid and lysine were previously reported to adopt stable α-helices in solution (Marqusee and Baldwin, 1987; Marqusee et al., 1989; Padmanabhan et al., 1991). The self-complementary oligopeptide-based biomaterial can alsobe processed into fibers. The liquid peptide dissolved in water can be injected into a salt solution via a needle to produce thread-like materials. Optionally, this material can be further processed into fibers or threads.

Length and Sequence of Membrane-forming Peptides

The effect of length and sequence on membrane formation was examined using several peptides (Table 1 and Example 3). The sixteen amino acid peptide, EAK16, with the sequence $(AEAEAKAK)_2$ (310–325 of SEQ ID NO: 2), could undergo self-assembly, while a twelve amino acid peptide, EAK12, with the sequence AEAKAEAEAKAK (SEQ ID NO: 24), was able to associate to a much smaller extent and formed small and non-uniform pieces of membranous material. EAK8, AEAEAKAK (310–317 SEQ ID NO: 2), which has a single unit of the repeat, did not form membranes under identical conditions. Another 16 amino acid amphiphilic peptide, RAD16, having the sequence $(RARADADA)_2$ (SEQ ID NO: 3), was found to form macroscopic membranes. Its 8 amino acid counterpart, RAD8, did not form macroscopic membranes. These results indicate that peptide length is an important factor in the formation of macroscopic membranes. The peptide length should be more than 12 amino acids and preferably at least 16 residues. Very long peptides, e.g., of about 200 amino acids, may encounter problems due to insolubility and intramolecular interactions which destabilize membrane formation. Furthermore, peptides with a large amount of hydrophobic residues may have insolubility problems. The optimal lengths for membrane formation will probably vary with the amino acid composition.

Four non-amphiphilic peptides of varying amino acid sequence were tested for membrane formation; these are β-amyloid (1–28) (SEQ ID NO: 4), β-amyloid (23–35) (SEQ ID NO: 5), substance P (SEQ ID NO: 6), and spantide (SEQ ID NO: 7). None of these peptides produced macroscopic membranes under the identical conditions used with EAK16 and RAD16 (Table 1). These results indicate that the alternating hydrophobic and hydrophilic self-complementary sequence of the peptide is important to membrane formation.

Figure 5A:
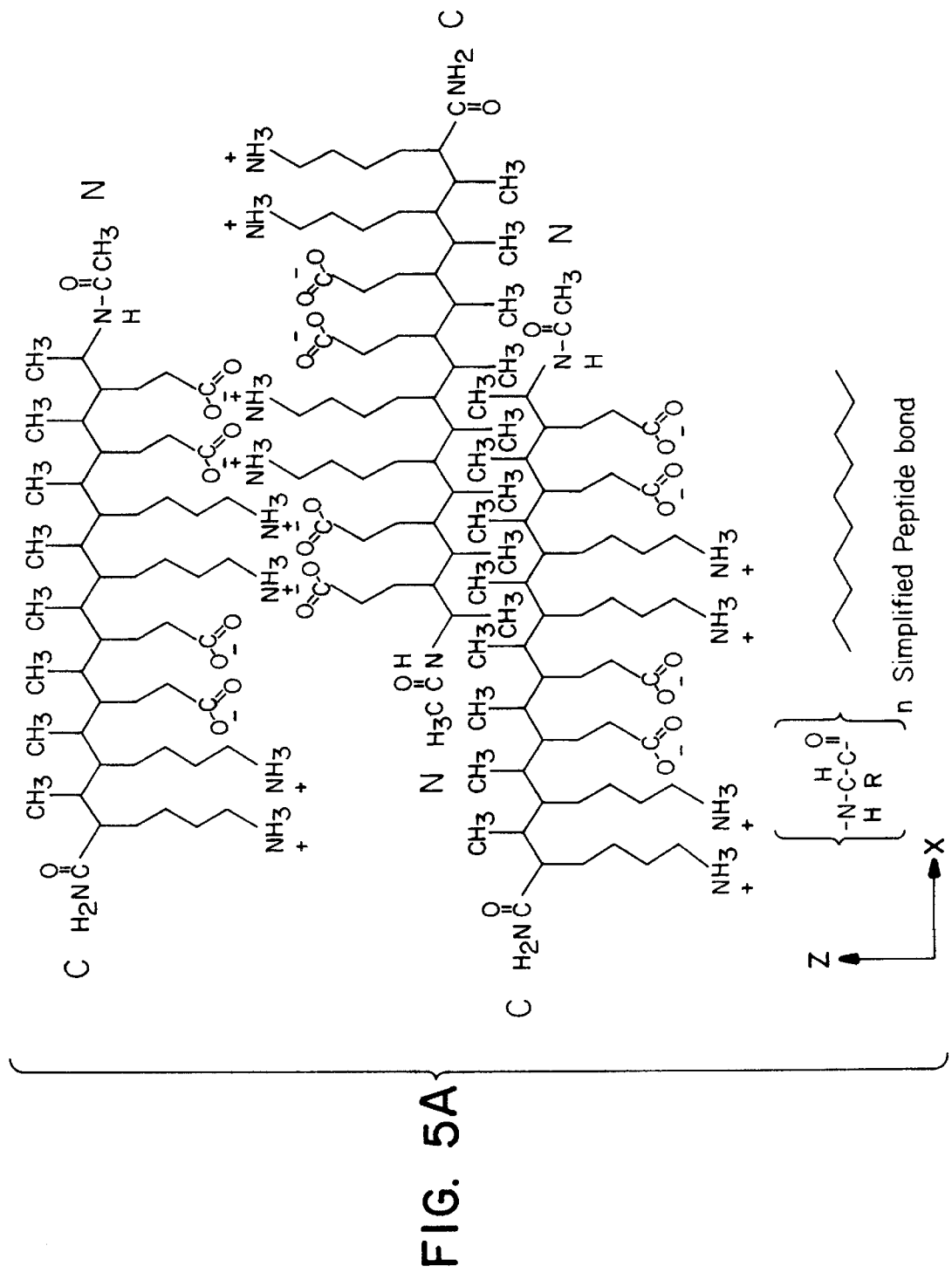
FIGS. 5A–5C show the hypothetical interactions between EAK16 molecules in the membranes and the secondary and tertiary structures resulting therefrom.

Consideration of these results leads to a molecular model in which intermolecular interactions between the peptides stabilize the secondary and tertiary structures of the membranes. Due to the alternating hydrophobic and hydrophilic residues of EAK16, β-sheets formed from EAK16 peptides can present a hydrophobic face and a hydrophilic face. The four glutamic acids of EAK16 have carboxyl side-chain groups with a pKa of 4.4–4.6 and the four lysines have amino side-chain groups with a pKa of 10.0–10.2. At neutral physiological, the side-chains of the glutamic acids and lysines are negatively and positively charged, respectively. FIG. 5A predicts interaction between three molecules of EAK16 peptide representing three antiparallel β-sheets. Two β-sheet layers are held together by hydrophobic interactions of alanine side-chains facing each other and two by ionized pair or salt bridge interactions between the charged lysines and glutamic acids facing each other. The structure can also be formed of parallel β-sheets. The tertiary structure comprising many β-sheets can be extended in the Z direction. In FIG. 5A, the peptides are staggered. The staggered arrangement allows extension of the structure in the X direction, along the peptide backbone.

Figure 5B:
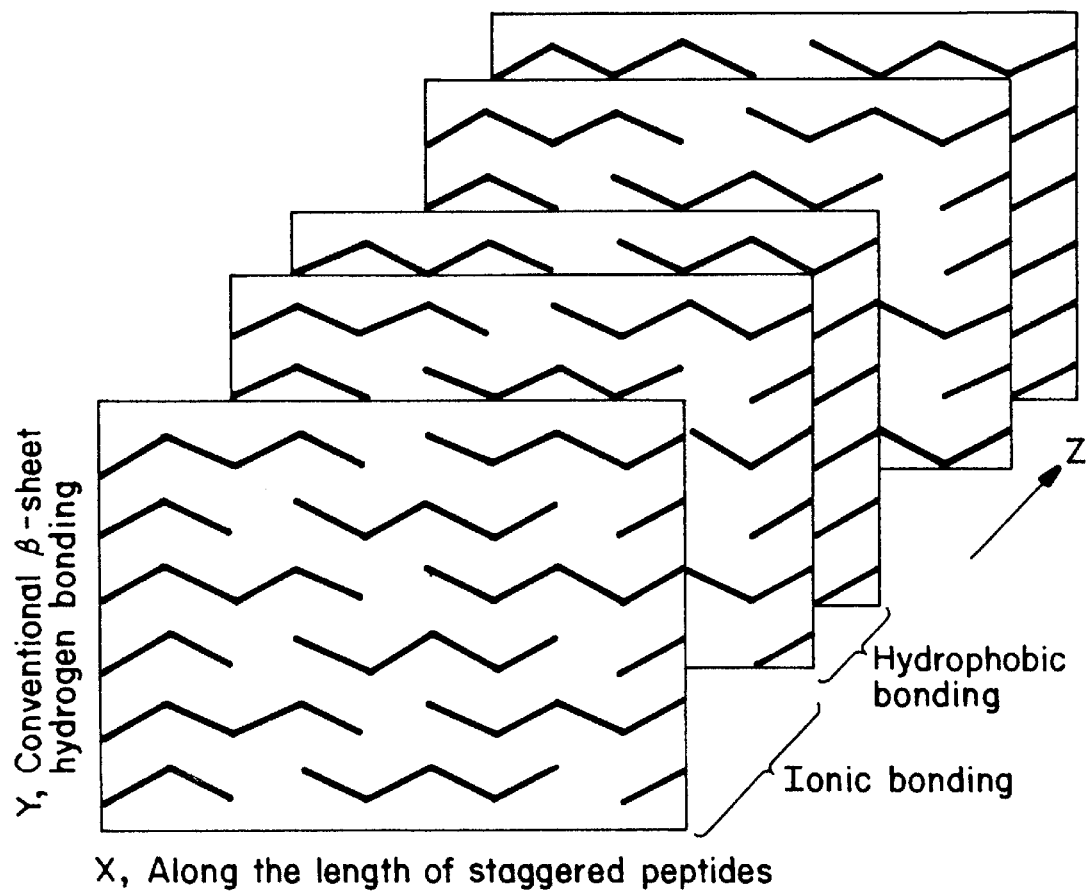

A three-dimensional view is shown in FIG. 5B. Each rectangle represents the plane of a β-sheet. In the Y dimension are the conventional β-sheet interactions, i.e., hydrogen bonding between the amino and carboxyl groups of the peptide backbones. In the X dimension, staggered coupling of the peptides within the β-sheets contributes to stability along the peptide backbone. In the Z dimension, interactions between β-sheets are stabilized by the extended ionized pair and hydrophobic interactions. The combination of these interactions are thought to result in the formation of β-barrel structures which may be the filaments observed under high magnification. The stagger distance between coupled peptides would determine the length of the filaments.

Figure 5C:
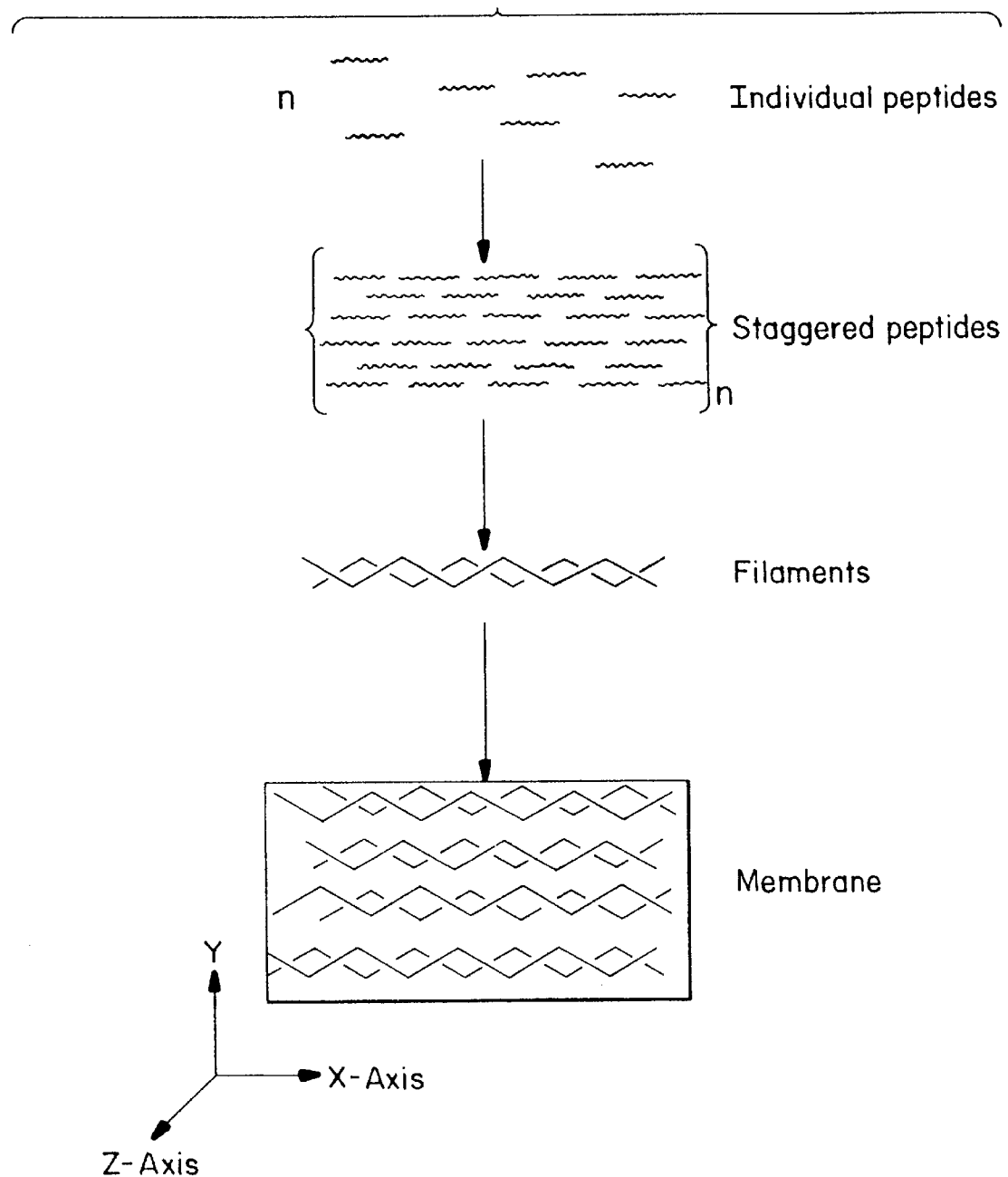

FIG. 5C illustrates the increasing levels of structural complexity as the peptides self-assemble into membranes.

Peptides which can form ionized pairs between their hydrophilic side-chains are referred to herein as complementary. Complementary pair interactions can also occur as a result of hydrogen bonding between the hydrophilic side-chains. Thus, Asn or Gln can function as hydrophilic amino acids in place of charged residues in membrane-forming peptides. Since ionized pair interactions are stronger than hydrogen bonds, peptides with acidic and/or basic amino acid side-chains would be expected to form more stable membranes than peptides with hydrogen bonding side-chains.

Figure 6A:
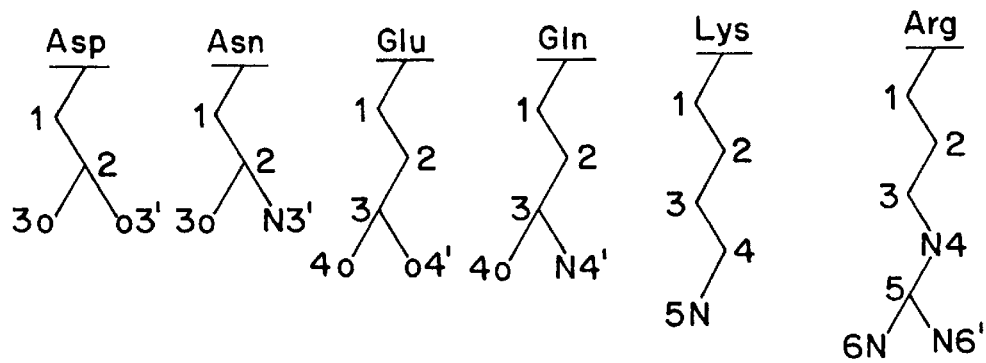
FIG. 6 illustrates calculation of the interpeptide distance of ionized and hydrogen bonding amino acid pairs.
Figure 6B:
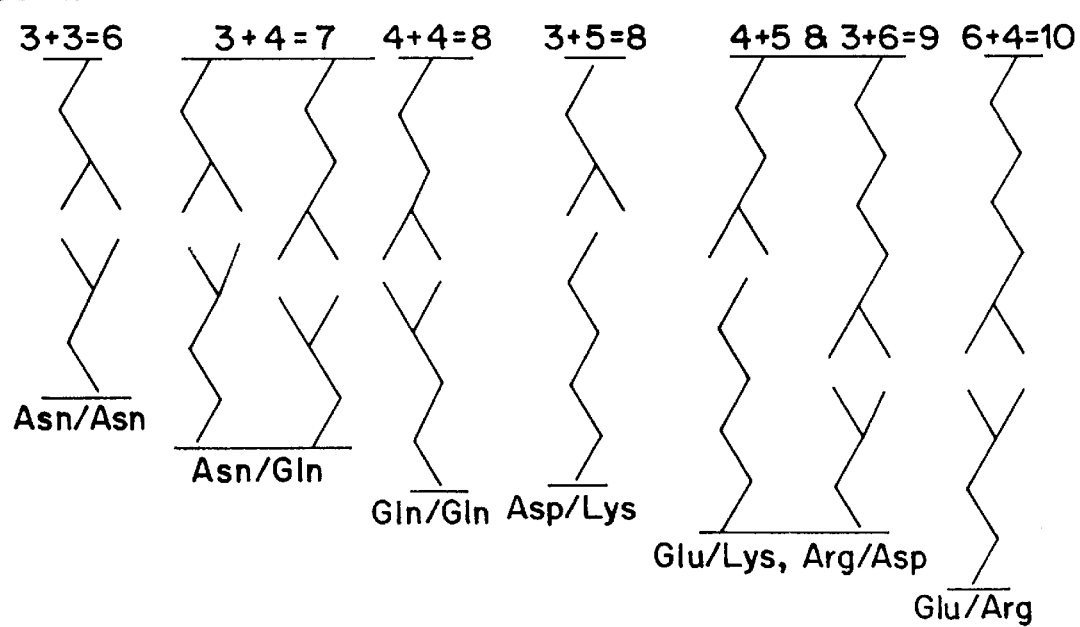

An additional stabilization factor is that complementary peptides maintain a constant distance between the peptide backbones. Peptides which can maintain a constant distance upon pairing are referred to herein as structurally compatible. The interpeptide distance can be calculated for each ionized or hydrogen bonding pair by taking the sum of the number of unbranched atoms on the side-chains of each amino acid in the pair (FIG. 6). For example, lysine has 5 and glutamic acid has 4 unbranched atoms on its side-chains, respectively. An intermolecular interaction between two EAK16 peptides would involve ionized pairing between the lysine amino group and the glutamic acid carboxyl group. The interpeptide distance for a lysine-glutamic acid pair would be 5+4=9 atoms. Since all the pairs in a EAK16—EAK16 interaction would be Lys-Glu, the interpeptide distance would be constant at 9 atoms along the length of the peptides (FIG. 7A). Thus, the EAK16 peptide is self-complementary and self-compatible, and homogeneous mixtures of EAK16 form membranes.

FIG. 7A illustrates a convenient way to check whether two peptide molecules are complementary and structurally compatible. Various possibilities for staggering the coupling of the peptides are illustrated in FIG. 7B.

Amphiphilic peptides which are greater than 12 amino acids long, self-complementary and self-compatible, are expected to self-assemble into macroscopic membranes in homogeneous peptide solutions. Two examples, EAK16 and RAD16, have been demonstrated. Table 2 lists some other peptides which are predicted to form membranes in homogeneous mixtures. These examples illustrate some of the variety of amino acid arrangement and composition of membrane-forming peptides.

The criteria of amphilic sequence, length, complementarity and structural compatibility apply to heterogeneous mixtures of peptides. Suppose that two different peptides are used to form the membranes: peptide A, VRVRVDVDVRVRVDVD (SEQ ID NO: 20), has Arg and Asp as the hydrophilic residues and peptide B, ADADAKAKADADAKAK (SEQ ID NO: 21), has Lys and Asp (FIG. 7C). Peptides A and B are complementary; the Arg on A can form an ionized pair with the Asp on B and the Asp on A can form an ionized pair with the Lys on B. A calculation of the interpeptide distances in such pairs (FIG. 6), however, shows that the two peptides are not structurally compatible. Using a conversion factor of 3 Å per atom, the difference in interpeptide distance between the two pairs would be 3 Å. Applicants estimate that a variation in interpeptide distance of more than 3–4 Å would destabilize intermolecular interactions leading to membrane formation. Thus, in a heterogeneous mixture of peptides A and B, membranes would likely form, but they would be homogeneously composed of either peptide A or B.

Using this sort of calculation, it becomes evident that a peptide containing both Asn and Gln as hydrophilic residues will probably form membranes in which the peptides are staggered and Asn-Gln (interpeptide distance=7) pairs are formed, but not Asn-Asn (distance=6) and Gln-Gln (distance=8) pairs.

Examples of peptides which are self-complementary and self-compatible, and thus, expected to form membranes in homogeneous mixtures, can be summarized in the following formulas:

$$(\Phi_i \Psi_j \Phi_k \Gamma_l)_n \qquad (1)$$

$$[(\Phi\Psi)_k (\Phi\Gamma)_l]_n \qquad (2)$$

where $\Phi$, $\Psi$, and $\Gamma$ represent neutral, positively and negatively, charged amino acids, respectively, which determine the composition and sequence; i, j, k, and l are integers and denote variable numbers; n denotes the numbers of repeating units which also determines the length of the oligopeptides.

The EAK16 polymer has alanine as its hydrophobic residue on one side of the sheet and clusters of two glutamates followed by two lysines on the ionic side. We refer to this pattern of two positive charges followed by two negative charges as Modulus 2. In this case, the formula (2) is applied where both k and l are 2. We could also imagine other peptides which have Modulus 1, i.e., alternations of positive and negative charges on one side of the β-sheet described by the formula (1), where i, j, k and l are 1, or Modulus 3 in which there are clusters of three negatively charged residues followed by three positively charged residues, etc, where k and l are 3 in the formula 92). The nature of the hydrophobic side chain on the other side of the sheet can also be varied.

Membranes can also be formed of heterogeneous mixtures of peptides, each of which alone would not form membranes, if they are complementary and structurally compatible to each other. For example, mixtures of (Lys-Ala-Lys-Ala)$_4$ (SEQ ID NO: 25) and (Glu-Ala-Glu-Ala)$_4$ (SEQ ID NO: 26) or of (Lys-Ala-Lys-Ala)$_4$ and (AlaAsp-Ala-Asp)$_4$ (SEQ ID NO: 27) would be expected to form membranes, but not any of these peptides alone due to lack of complementarity.

Peptides, which are not perfectly complementary or structurally compatible, can be thought of as containing mismatches analogous to mismatched base pairs in the hybridization of nucleic acids. Peptides containing mismatches can form membranes if the disruptive force of the mismatched pair is dominated by the overall stability of the interpeptide interaction. Functionally, such peptides can also be considered as complementary or structurally compatible. For example, a mismatched amino acid pair may be tolerated if it is surrounded by several perfectly matched pairs on each side. Mis-matched peptides can be tested for ability to self-assemble into macroscopic membranes using the methods described herein.

In summary, peptides expected to form macroscopic membranes have alternating hydrophobic and hydrophilic amino acids, are more than 12 amino acids and preferably at least 16 amino acids long, are complementary and structurally compatible. The amino acids can be selected from d-amino acids, l-amino acids, or combinations thereof. The hydrophobic amino acids include Ala, Val, Ile, Met, Phe, Tyr, Trp, Ser, Thr and Gly. The hydrophilic amino acids can be basic amino acids, e.g., Lys, Arg, His, Orn; acidic amino acids, e.g., Glu, Asp; or amino acids which form hydrogen bonds, e.g., Asn, Gln. Acidic and basic amino acids can be clustered on a peptide, as in EAK16 and RAD16. The carboxyl and amino groups of the terminal residues can be protected or not protected. Membranes can be formed in a homogeneous mixture of self-complementary and self-compatible peptides or in a heterogeneous mixture of peptides which are complementary and structurally compatible to each other. Peptides fitting the above criteria can self-assemble into macroscopic membranes under suitable conditions (described below).

The term peptides, as used herein, includes polypeptides and oligopeptides. The peptides can be chemically synthesized or they can be purified from natural and recombinant sources.

For example, the macroscopic membrane can be formed by self-assembly of a peptide having the sequence (Ala-Glu-Ala-Glu-Ala-Lys-Ala-Lys)$_n$ (SEQ ID NO: 2 (aa 310–325) or (Arg-Ala-Asp-Ala-Arg-Ala-Asp-Ala)$_n$ (SEQ ID NO: 40 (aa 1–8), where n is greater than or equal to 2.

Formation of the Macroscopic Membranes and Filaments

The novel self-assembly of EAK16 was initially observed in tissue culture medium (Dulbecco Modified Eagle's Medium, Gibco BRL, Gaithersburg, Md.) containing calf serum. Membranes can also form from EAK16 in phosphate-buffered saline (PBS: 150 mM NaCl, 10 mM sodium phosphate, pH 7.4). Macroscopic membranes do not form in water but appear after addition of sodium phosphate to a water-peptide solution to an approximate final concentration of 100 mg/ml. Thus, salt appears to play an important role in the self-assembly process.

Various metal cations were tested for effectiveness at inducing membrane formation from EAK16. The results indicate that monovalent metal cations induce membrane formation, but divalent cations primarily induce unstructured aggregates. Some anions, acetate, Cl$^-$, $SO_4^{-2}$, and $PO_4^{-2}$, and organic ions, $NH_4^+$ and Tris-Cl, were also tested and were not found to induce membrane formation.

The order of effectiveness of the monovalent cations appears to be Li$^+$>Na$^+$>K$^+$>Cs$^+$. Cs$^+$ produces the least amount of membranes and in addition, yields nonmembranous precipitates. The effectiveness of the monovalent cations appears to correlate inversely with the crystal radii of the ions: Li$^+$ (0.6 Å), Na$^+$ (0.95 Å), K$^+$ (1.33 Å), and Cs$^+$ (1.69 Å) (Pauling, 1960). A correlation is also seen with the hydrated radii of the ions: Li$^+$ (3.4 Å), Na$^+$ (2.76 Å), K$^+$ (2.32 Å), and Cs$^+$ (2.28 Å), and with the order of enthalpies of the monovalent cations (Pauling, 1960). It is not known at present if the monovalent metal cations act as a catalyst or if they are incorporated into the membrane. The size of the filaments (10–20 nm) and interfilament distance (50–80 nm) in the membranes formed from EAK16 suggest that hydrated ions may stabilize the intermolecular interaction.

Concentrations of monovalent metal cations (NaCl) as low as 5 mM and as high as 5M have been found to induce membrane formation within a few minutes. Thus, membrane formation appears to be independent of salt concentration over this wide range. Salt concentrations of less than 5 mM may also induce membrane formation, but at a slower rate.

The initial concentration of the peptide is a significant factor in the size and thickness of the membrane formed. In general, the higher the peptide concentration, the higher the extent of membrane formation. Membranes can form from initial peptide concentrations as low as 0.5 mM or 1 mg/ml. However, membranes formed at higher initial peptide concentrations (about 10 mg/ml) are thicker and thus, likely to be stronger. Therefore, it is preferable when producing the membranes to add peptide to a salt solution, rather than to add salt to a peptide solution.

Formation of the membranes is very fast, on the order of a few minutes, and seems to be irreversible (see below). The process is unaffected by pH$\leq$12 (the peptides tend to precipitate out at pH above 12), and by temperature. The membranes can form at temperatures in the range of 4 to 90° C.

Formation of the membranes is inhibited by the presence of divalent metal cations at concentrations equal to or greater than 100 $\mu$M, which promote unstructured aggregation rather than membrane formation, and by sodium dodecyl sulfate (SDS) at a concentration of at least 0.1%.

Properties of the Macroscopic Membranes

Once formed, the macroscopic membranes are stable in a variety of aqueous solutions, including water, phosphate-buffered saline (PBS), tissue culture medium, serum, and also in ethanol, and can be transferred to and stored in any of these liquids. Membranes formed of EAK16 and RAD16 have been found to be stable in water or PBS for at least a week without any sign of deterioration. The membranes can be transferred from one solution to another using a solid support such as a spatula. They can be broken by cutting, tearing or shearing.

Membranes formed of EAK16 were found to be unusually stable under various conditions expected to disrupt them. Circular dichroism (CD) spectroscopy measurements further demonstrated the unusual stability of the β-sheet secondary structure of the peptide EAK16 (Example 4). The β-sheets can be thought of as the building blocks for the macroscopic membrane structures and their unusual stability confirms the strength of the peptide interactions holding the membrane together.

Figure 8A:
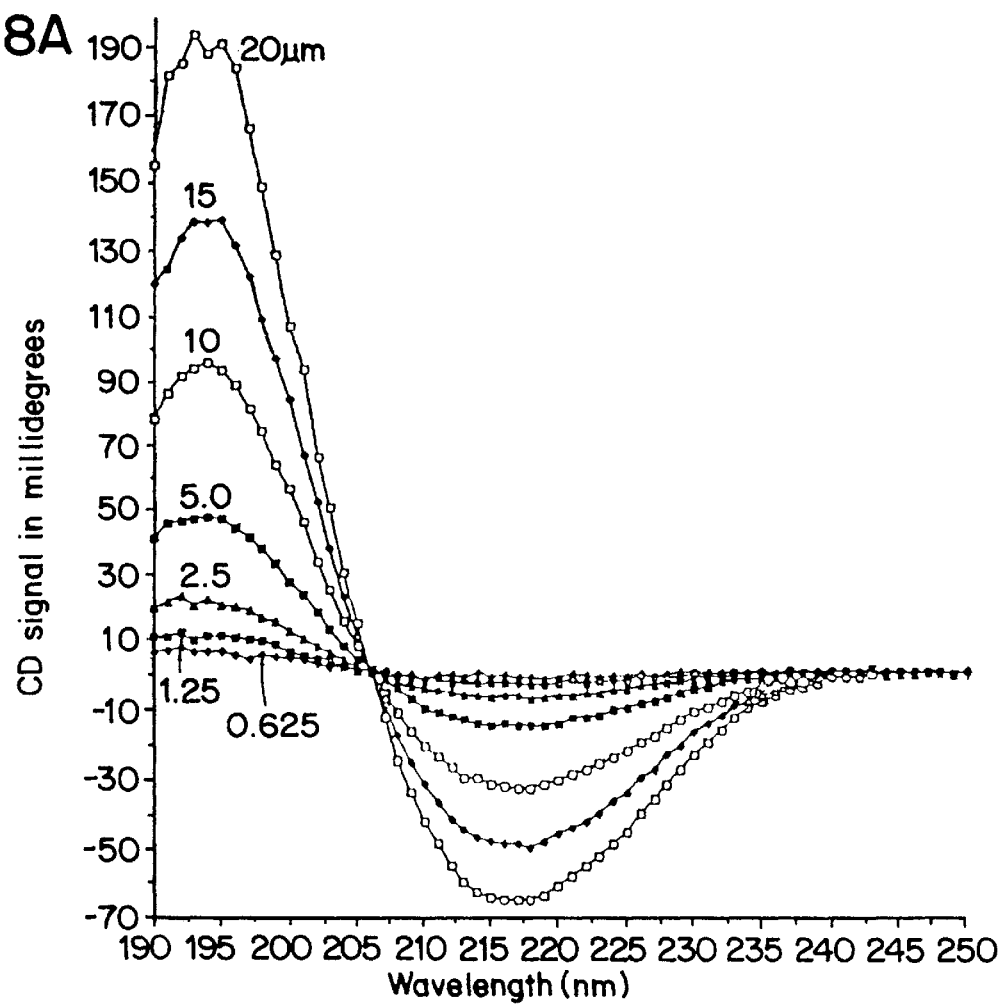
FIGS. 8A and 8B show the stability of the β-sheet structure of peptide EAK16 in water at different peptide concentrations.
Figure 8B:
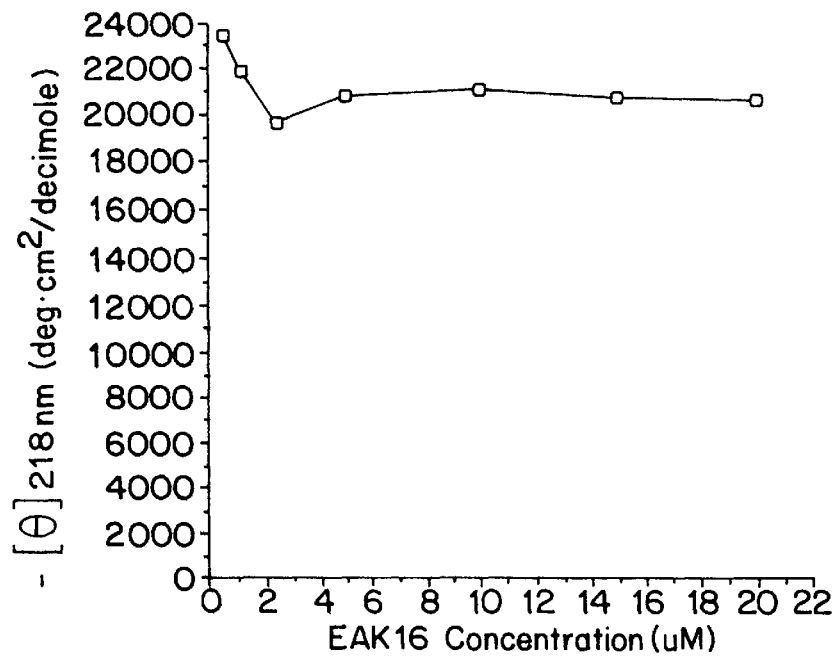

The β-sheet structure of EAK16 was not significantly affected by dilution of the peptide, as seen in FIGS. 8A and 8B. FIG. 8A shows the CD spectra of EAK16 at 0.625, 1.25, 2.5, 5.0, 10, 15 and 20 $\mu$M peptide concentrations in water. The Y axis is expressed as CD signal in millidegrees in order to show the β-sheet stability of the peptide in diluted concentrations. These data show that, even at the lowest concentration (0.625 $\mu$M), the characteristic β-sheet CD spectrum with minimum at 217 nm and maximum at 194 nm was still clearly recorded. The CD signal is linearly proportional to the peptide concentration, suggesting that the β-sheet structure is stable in very dilute concentrations. Note that the spectra cross an isosbectic point at 205 nm, thus, indicating that the same structures exist at all the peptide concentrations. FIG. 8B shows a plot of normalized peptide concentrations from 0.625 to 20 $\mu$m vs. the mean residue ellipticity at 218 nm. The stability of the β-sheet structure of EAK16 at very dilute concentrations of the peptide contrasts with observations of other β-sheet forming peptides, such as β(29–42) and β(1–42) of the β-amyloid protein (Barrow and Zagorski, 1991) and the TL-LRR1 peptide (23 residue length) from the toll protein of Drosophila (Gay et al., 1991), which show a stable β-sheet only in high peptide concentrations.

The stability of the membranes was also tested under a range of temperature, pH and chemical conditions. For these experiments, membranes were formed by adding 20 μl of a 0.5 mM stock solution of EAK16 to 0.5 ml of PBS, and transferred into water or other solutions at test conditions.

Figure 9A:
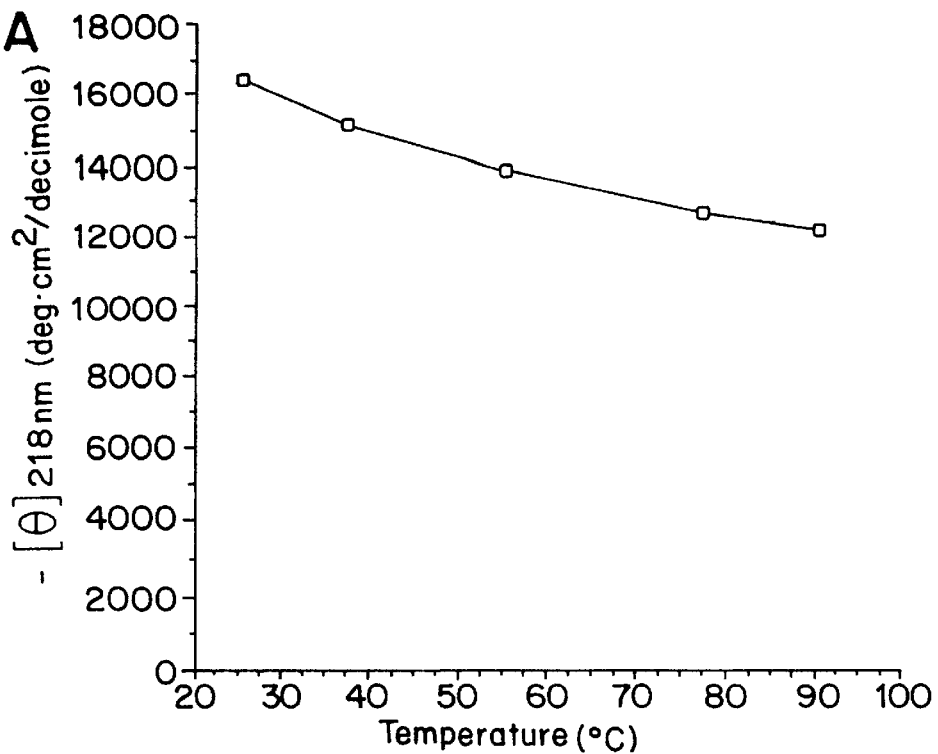
FIGS. 9A and 9B show the thermal stability of the β-sheet structure of EAK16.
Figure 9B:
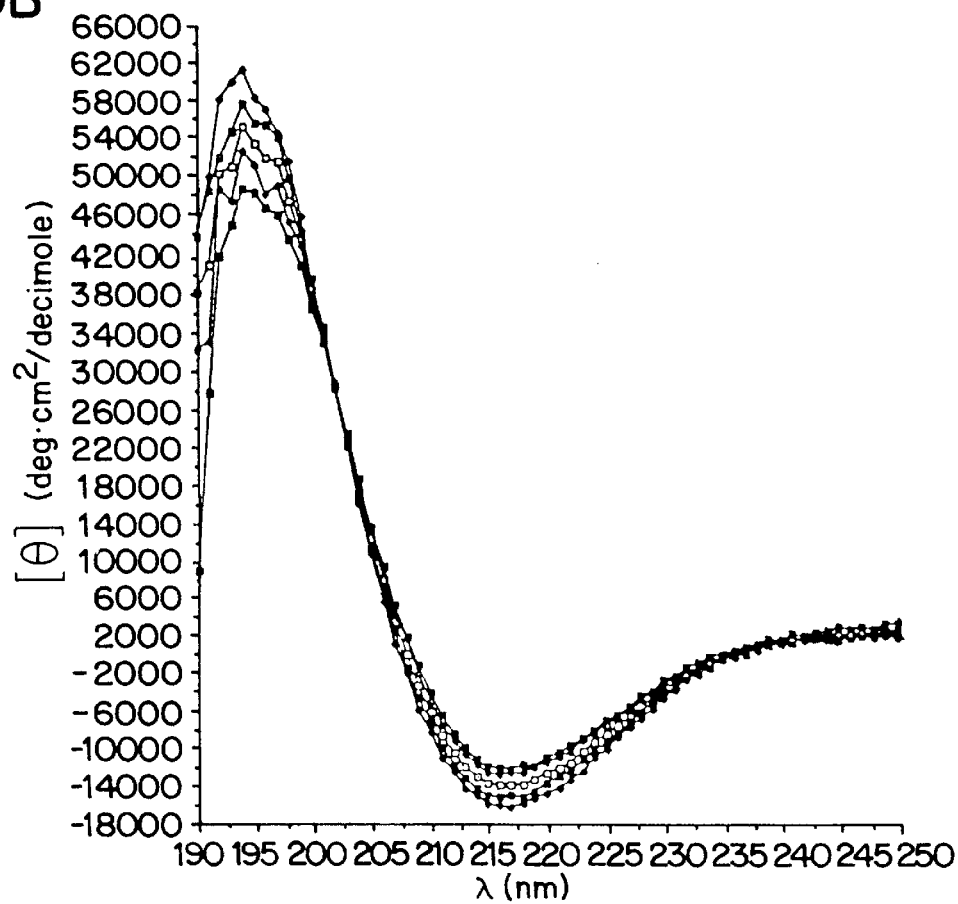

The membranes were found to be stable in water over a wide range of temperatures: up to 95° and at 4°,–20°, and –80° C. The membranes could be frozen and thawed, although care was required in handling the frozen membranes which were brittle. In boiling water, the membranes tended to be sheared by the mechanical agitation. The CD spectra of EAK16 were also found to be unaffected over the range of 25–90° C. (FIGS. 9A and 9B). FIG. 9B shows the CD spectra of EAK16 (8 μM) at 25, 37, 55, 70 and 90° C. The thermal profile of EAK16 (FIG. 9A) shows a 22% decrease of mean residue ellipticity over this range. Such strong thermal stability of the defined β-sheet structure of EAK16 is unusual for a small peptide. For example, these findings contrast with the α-helix-forming sixteen residue (Ala, Glu, Lys)-containing peptides studied previously (Marqusee and Baldwin, 1987).

The EAK16 membranes were also tested in water at pH 1.5, 3, 7 and 11 at room temperature for at least a week and at 95° C. for about 4 hours. The membranes were unaffected at these pH. The β-sheet structure of the peptide was also unaffected over this pH range; the pH profile (FIG. 10) shows a less than 10% decrease of ellipticity. Precipitation of the peptide was observed at pH above 12.5. These findings suggest that the overall β-sheet structure of EAK16 is not altered drastically in various pH even though charged residues would be neutralized under such conditions. It is possible that the complementary interactions between the Glu and Lys side-chains are strong even when the carboxyl groups of the Glu residues have been protonated at pH 1.5 and 3, due to their ability to form hydrogen bonds even when protonated.

The EAK16 membranes were further tested for resistance to chemical denaturation under the following conditions: 1% and 10% sodium dodecyl sulfate (SDS); 1, 2, 3, 4, 5, 6 and 7M guanidine-HCl; and 1, 2, 3, 4, 5, 6, 7 and 8M urea. The membranes remained stable in the presence of these chemicals at room temperature for at least 4 days. The membranes were also tested at 95° C. for 4 hours in 10% SDS; 7M guanidine-HCl; and at 8M urea. At this temperature, the membranes dissolved in 8M urea, but remained intact in SDS and 7M guanidine-HCl.

Figure 11:
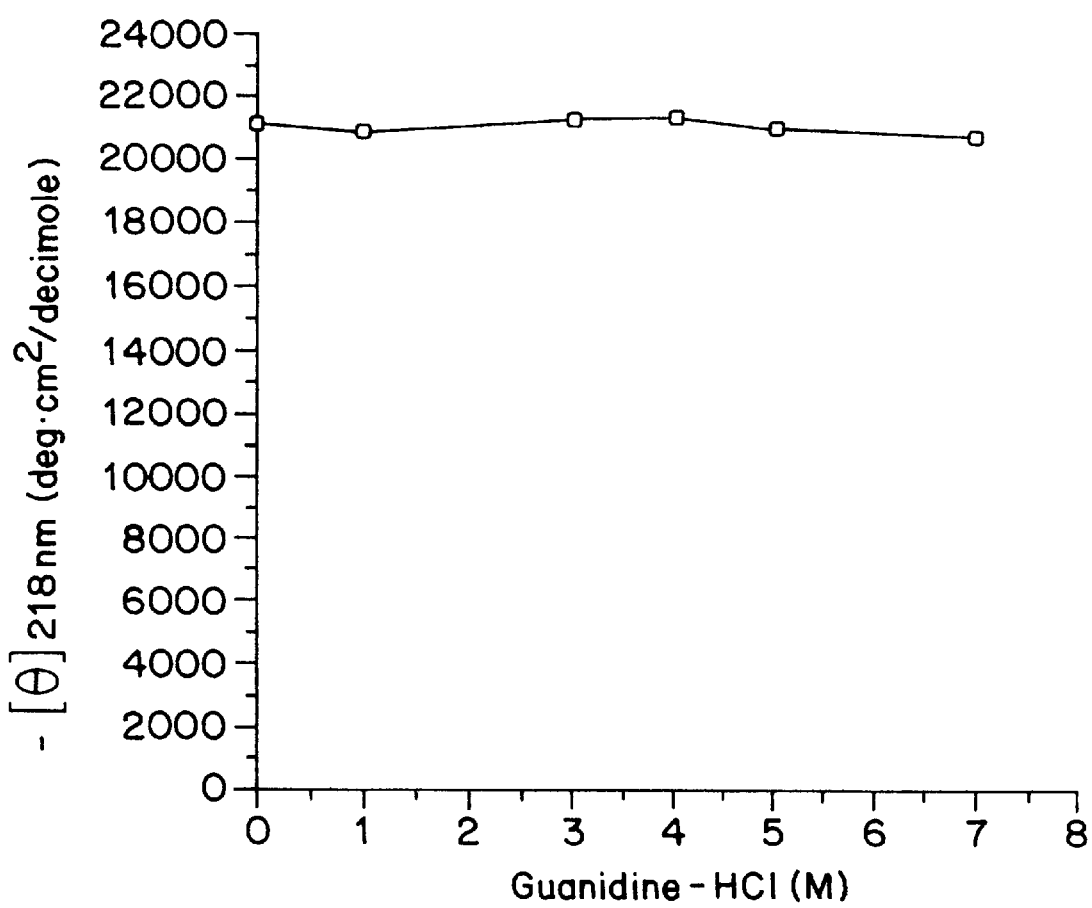
FIG. 11 shows the stability of the β-sheet structure of EAK16 in guanidine-HCl.

CD spectra measurements also showed that the β-sheet structure of EAK16 was not significantly affected by incubation in 0.1% SDS at 90° C., 1–7M guanidine-HCl at room temperature or 8M urea at room temperature for over 16 hours. No significant differences in CD signals were observed even under the strongest denaturing conditions of 7M guanidine-HCl (FIG. 11) and 8M urea. This is surprising, since 7M guanidine-HCl and 8M urea can effectively denature most proteins and proteinaceous aggregates, including other β-sheet forming peptides (Trudelle, 1975). Furthermore, these denaturants are expected to diminish hydrogen bonds and hydrophobic interactions. The stability of the EAK16 secondary structure suggests that the peptide molecules strongly interact to form an interwound β-sheet structure. This is consistent with the interwound filamentous structures observed in the presence of monovalent alkali salts.

The peculiar stability of the secondary and tertiary structure of EAK16 observed may be explained by the additive stabilizing interactions illustrated by FIG. 5. It is known from theoretical calculations that each ionic bond can contribute approximately 5 Kcal/M and that the interaction of apolar side-chains of alanines can contribute 1 Kcal/M. The hydrogen bonds between C=O and the N in the backbone of peptides can also contribute approximately 3 Kcal/M. Therefore, EAK16 would have a total interaction energy of about 72 Kcal/M per two molecules. Since the β-sheets are staggered and over-layed, the additive interaction energy is much greater than that of individual molecules. The peptide bond itself has only 5–7 Kcal/M and is very stable. In addition, the hydrophobic and hydrophilic interactions between β-sheets seem to stabilize the secondary structure under conditions in which β-sheets are usually disrupted. Thus, it appears that even under very harsh conditions, the stabilization energy of these membrane-forming peptides is greater than the disruption energy.

It is interesting to note that the EAK8 and EAK12 peptides do not have such unusual stability. EAK8 exhibited a random coil structure under identical conditions. EAK12 was found to denature from a β-sheet structure at high temperatures, and to subsequently undergo reversible helix-coil transitions. This is consistent with our model, in which stabilization in the direction of the peptide backbone (X dimension, FIG. 5) is also significant.

Further analysis by methods such as fiber X-ray diffraction and atomic force microscopy may provide more insights into the organization and stabilization of the membrane structure.

The membranes and filaments also have some interesting and useful biological properties. They are highly resistant to digestion by proteases. Membranes and filaments formed from EAK16 were not degraded by trypsin, α-chymotrypsin, papain, protease K, or pronase at 100 μg/ml concentration in the appropriate buffers when incubated at 37° C. overnight or at room temperature (25° C.) for a week, even though the EAK16 peptide contains potential protease cleavage sites.

The membranes also appear to be non-cytotoxic. The EAK16 peptide formed macroscopic membranes when added to a tissue culture of nerve growth factor-differentiated rat PC12 cells. The peptides and resultant membranes did not affect the appearance or rate of growth of the cells.

Uses of the Macroscopic Membranes and Filaments

The above-described macroscopic membranes and filaments have several uses. Because they are stable in serum, resistant to proteolytic digestion and alkaline and acidic pH, and are non-cytotoxic, these membranes and filaments are useful in biomaterial applications, such as medical products (e.g., sutures), artificial skin or internal linings, slow-diffusion drug delivery systems supports for in vitro cell growth or culture and supports for artificial tissue for in vivo use. The membranes can be made and stored in a sterile condition. For example, they can be produced using synthetic peptides and sterile PBS and stored in sterile PBS. The membranes can also be stored in a water/ethanol solution. In addition, the membranes have a simple composition and can be easily and relatively inexpensively produced in large quantities. They can be used in numerous applications in which permeable and water insoluble material are appropriate, such as separation matrices (e.g., dialysis membranes, chromatographic columns).

Due to their permeability, the membranes described herein are useful as slow-diffusion drug delivery vehicles for protein-type drugs, including erythropoietin, tissue type plasminogen activator, synthetic hemoglobin and insulin. The drug could be wrapped in layers of membrane, which would permit slow release of the drug and may extend the half-life of the drug in the blood-stream. Because the membranes are resistant to degradation by proteases and stomach acid (pH 1.5), drug delivery vehicles made of these membranes could be taken orally.

The extremely small pore size of the membranes may make them useful as filters, for example, to remove virus and other microscopic contaminants (see e.g., Erickson, 1992). The pore size (interfilament distance) and diameter of the filaments in the membranes can be varied by varying the length and sequence of the peptides used to form the membranes.

In view of the conductive nature of histidine, membranes and filaments manufactured with the amino acid, histidine, will be useful as a conductive biopolymer.

Modification of the membranes may give them additional properties. For example, the membranes may be further strengthened by cross-linking the peptides after membrane formation by standard methods. Collagen may be combined with the peptides to produce membranes more suitable for use as artificial skin; the collagen may be stabilized from proteolytic digestion within the membrane. Furthermore, combining phospholipids with the peptides may produce vesicles.

The membranes may also be useful for culturing cell monolayers. Cells prefer to adhere to non-uniform, charged surfaces. The charged residues and conformation of the proteinaceous membranes promote cell adhesion and migration. The addition of growth factors, such as fibroblast growth factor, to the peptide membrane can further improve attachment, cell growth and neurite outgrowth.

Cells were observed to adhere to EAK16 membranes floating in the tissue culture dish. Cell attachment occurs through direct interactions with the biopolymer membrane as shown by attachment in serum-free medium and cyclohexamide treatment of cells. Cell attachment to biopolymer membranes is robust in $Ca^{++}$ and $Mg^{++}$ free, EDTA containing medium, which indicates that the attachment phase is integrin independent.

Certain peptide polymers of this class contain sequences which are similar to the cell attachment ligand RGD. The suitability of these biomaterials for supporting in vitro cell growth was tested by introducing a variety of cultured primary and transformed cells to homopolymer sheets of EAK16, RAD16, RADA16, and heteropolymers of RAD16 and EAK16. The RAD-based peptides are of particular interest because the similarity of this sequence to RGD. The RAD sequence is a high affinity ligand present in the extracellular matrix protein tenascin and is recognized by integrin receptors.

In addition, the permeability of the membranes would permit diffusion of small molecules, such as growth factors or peptide hormones, to the underside of cell monolayers, thus, presenting the potential for tissue culture of differentiated cells and/or stratified cell layers.

Cells can be grown in culture and can be engineered to produce valuable products (e.g., growth factors, interferon). These systems are known to offer many advantages over harvesting such products from animals. Many cells require adherence to a surface, such as tissue culture plastic, resulting in a surface-to-volume limitation. The biopolymer materials of the present invention, containing cells, can be stacked in a vessel containing culture medium, improving the density of cells grown in this manner. The porous microstructure of the biopolymers can also be useful for encapsulating cells. The pore size of the membrane can be large enough to allow the diffusion of cell products and nutrients. The cells are, generally, much larger than the pores and are, thus, contained.

A wide variety of cells can grow on these biopolymers. This indicates that artificial tissues can be grown in vitro using biopolymer substrates. Evidence indicates that the EAK16 biopolymers are not antigenic (e.g., do not provoke an immune response). While other polymers based on organic chemicals and silicone have been used for transplantation purposes, many of these materials can degrade into hazardous components. In contrast, the degradation of our oligopeptide biopolymers yields amino acids, which are non-toxic and can be utilized by tissues to make proteins.

The filamentous structure of the membranes and filaments described herein is similar to the structure of silk fibroin protein, which consists largely of glycine-alanine-serine or alanine-glutamine repeats and forms stable $\beta$-sheet filaments, although the silk fibroin protein has a molecular weight greater than 360,000 (Lizardi, 1979), whereas EAK16 has a molecular weight of only 1,760. The filaments formed by EAK16 are much finer than silk fibers. The membranes formed by EAK16 and other amphiphilic peptides described herein can be useful for making very thin, transparent fabric.

In addition, it is interesting that the neurofibrillary tangles and amyloid plaques associated with neuropathological conditions, such as Alzheimer's disease, are salt-dependent aggregates of $\beta$-amyloid protein with extremely stable and highly insoluble $\beta$-sheet structure (Iqbal and Wisniewski, 1983). The aggregated Alzheimer's filament has a diameter of approximately 10–15 nm (Hilbich et al., 1991; Iqbal and Wisniewski, 1983; Halverson et al., 1990; Kirschner et al., 1987), similar to the dimensions of the EAK16 peptide filaments. Ordered filamentous aggregates (approximately 7–10 nm in diameter) have also been reported in another $\beta$-sheet forming peptide, TL-RR1, a 23 amino acid peptide segment found in the Drosophila Toll protein (Gay et al., 1991). Moreover, the scrapie prion protein also stains with Congo Red and forms aggregated filaments which are extremely stable and resistant to proteases. Thus, the formation of the macroscopic membranes may provide a useful model system for investigating the properties of biological proteins structures with such unusual properties as extreme insolubility and resistance to proteolytic digestion. Studies in such a model system may provide insights into the pathology and potential treatment of conditions characterized by the presence of these proteins or proteinaceous structures. For example, drugs which inhibit the self-assembly of the EAK16 peptide or other membrane-forming peptide into filaments or filamentous membranes can be identified. Drugs identified by such a method may be useful for treating Alzheimer's disease or scrapie infection.

The invention further relates to the regeneration of nerves with filaments of the membranes of the present invention. Nerve regeneration can be promoted and directed by transplanting filaments of RAD16 along the correct path to their targets. This would be extremely useful for patients with severed peripheral nerves. Such a technology could be refined to help people with spinal cord injuries. Neurite outgrowth of NGF differentiated PC12 cells, retonic acid-differentiated human neuroblastoma and mouse cerebellum granule cells occurs on RAD16-based biopolymers, but not on EAK16-based biopolymers, indicating that there is substrate specific support for such specialized functions.

In addition, the ability of small peptides such as EAK16 to self-assemble into membranes may be useful in origin of life studies related to cell membranes and cellular compartmentalization. Apropos to this sort of investigation is the interesting observation that the EAK16 peptide shows partial nucleotide hydrolysis activity. This activity is probably due to the ability of lysine and glutamic acid side-chains to perform general acid and base catalysis.

Zuotin

The sequence of EAK16 was originally found in a yeast protein called zuotin. zuotin was identified by its ability to bind preferentially to left-handed Z DNA in a gel shift assay developed by Applicants. The zuotin gene, ZUO1, was cloned and sequenced SEQ ID NO: 1). ZUO1 was found to encode a 433 amino acid protein having several interesting features. In addition to the alternating alanine and charged residues of the EAK16 sequence, the protein contains several potential phosphorylation sites (FIG. 1), including sites recognized by the CDC28 (or cdc2) kinase (⊗), casein kinase II (○), cAMP-dependent protein kinase (▼), tyrosine kinase (★), and protein kinase C (●). Zuotin also contains a bipartite nuclear targeting sequence.

Two distinct regions of zuotin were found to be similar to known proteins. One region (residues 111–165) was similar to *E. coli* DnaJ, yeast YDJ1, yeast SCJ1, yeast SIS1, SEC63 (or NLS1), avian polyomavirus small t and large T antigens, Drosophila csp29 and csp32, and human HDJ-1. A second region (residues 300–363) of zuotin is similar to several histone H1 variants, including some human, chicken and sea urchin variants.

Both partially purified yeast zuotin and bacterially expressed recombinant zuotin exhibited a high affinity for DNA in the left-handed Z conformation. The region of zuotin from amino acids 306 to 339 (heavily underlined in FIG. 1) is thought to be the DNA-binding domain. Mutational analysis showed that ZUO1 is not an essential gene, but that disruption of its function leads to slow cell growth.

The partial purification of the putative Z-DNA binding protein from yeast *S. cerevisiae*, the cloning and characterization of its gene and functional analysis are further described in Example 5.

The following examples illustrate the invention further and more specifically.

EXAMPLE 1

Peptide Synthesis, Purification, and Solubility

The peptides were synthesized by solid-phase peptide synthesis on an Applied Biosystems Model 430A peptide synthesizer coupler using standard N-tert-buty-oxycarbonyl (t-Boc) chemistry and cycles using n-methyl-pyrolidone (NMP) chemistry (Steward and Young, 1984). Both N- and C-termini of the peptide EAK16 were blocked to resemble its native state in the protein zuotin. The C-terminal amides were synthesized on p-methylbenzhydrylamine resin and the N-terminus of the peptide was acetylated using acetic acid anhydride with an equivalent of diidopropylethylamine (DIEA) in dimethylformamide. The peptides were cleaved from the resin using hydrofluoric acid/anisole 10:1 (v/v) (Applied Biosystems, 1986).

The peptides were purified through HPLC (high pressure liquid chromatography) using a Vydac $C_{18}$ semipreparative column, eluted with a gradient of 5–60% acetonitrile in 0.1% trifluoroacetic acid (TFA), and lyophilized in a speed vacuum. Peptide purity was determined by analytic HPLC and the composition was determined by amino acid analysis.

EAK16 peptide stock solutions were prepared at a concentration of approximately 0.57 mM (1 mg/ml) in water. The molecular weight of EAK16 is 1,760. EAK16 has a maximal solubility of 3 mM (about 5 mg/ml) in water, but can be solubilized at up to 6 mM (about 10 mg/ml) in 23% actonitrile. The concentration was determined by the ninhydrin methods using internal controls.

EXAMPLE 2

Circular Dichroism Measurement

Circular dichroism (CD) spectra were taken on an Aviv Model 60DS spectropolarimeter using program 60HDS for data processing. Because EAK16 contains both positively and negatively charged residues, the peptide itself can serve as a buffer. CD samples were prepared and measured at 25° C., unless otherwise indicated. All reagents were ultrapure and solutions were filtered through a 0.22 $\mu$M pore filter before use.

EXAMPLE 3

Preparation and Testing of Peptides for Membrane Formation

The EAK16, EAK12, and EAK8 peptides were synthesized by a peptide synthesizer (Applied Biosystems) and purified by reverse phase HPLC and eluted by a linear gradient of 5–80% acetonitrile, 0.1% TFA. The concentration of the peptides was determined by dissolving dried peptide in solution (w/v) and centrifuging the solution. Then, a portion of the solution was analyzed by hydrolysis with internal controls. The sequence of the peptides were confirmed by microsequencing (Edman degradation) using the Applied Biosystems peptide sequencer (Steward and Young, 1984; Applied Biosystems, 1986). The compositions of the peptides were confirmed by hydrolytic analysis.

Substance P, Spantide, and β-amyloid (1–28) are available from Bachem. β-amyloid (1–28) was also described in Barrow and Zagorski (1991). Substance P, Spantide, and β-amyloid (25–35) were aminylated on the C-terminal ends.

The EAK12 and EAK16 tested for membrane formation were acetylated and aminylated at both N- and C-terminal ends. Blocking of both of the N- and C-termini of EAK16 appeared not to be essential for membrane formation. The peptides were initially dissolved in water (5 mg/ml) or in 23% acetonitrile (10 mg/ml). A volume of 5–10 microliters of the dissolved peptides were applied to the DMEM medium, PBS or water. The formation of the membrane was first observed under a phase-contrast microscope and then, by the naked eye after staining with Congo Red.

EXAMPLE 4

Stability of The β-Sheet Structure of EAK16

Circular dichroism (CD) spectroscopy was used to monitor the stability of the β-sheet structure of EAK16 under various conditions.

Dilute peptide concentrations. EAK16 secondary structure was found to be stable in very dilute concentrations of the peptide. A 3 mM stock EAK16 solution was mixed in water to a concentration of 20 $\mu$M, allowed to equilibrate, and the CD spectrum measured. The solution was then diluted five times by two-fold serial dilutions to final concentrations of 15, 10, 5.0, 2.5, 1.25 and 0.625 µM, allowed to equilibrate and CD spectra taken. Reverse experiments, in which the concentration of peptide was increased by adding more peptide, were also done and similar results were obtained.

Temperature. The CD spectra of 8 µM EAK16 at 25, 37, 55, 70 and 90° C. in water were measured. The ratios of ellipticity at 194 nm/217 nm remained approximately 4.0 over the temperature range of 25–90° C. (Table 3); such a high ratio suggests strong stability of the β-sheet structure. The secondary structure of EAK16 was not substantially altered over this range of temperature and an isosbectic point was observed at 202 nm. The thermal profile showed a 22% decrease of $-[\theta]_{218\,nm}$ deg. cm²/decimole (FIG. 9).

pH. The β-sheet structure of EAK16 was also not significantly affected by pH. The peptide consists of 4 positively charged lysine and 4 negatively charged glutamic acid residues at neutral pH. Lysine has a calculated pKa of 10.0 and glutamic acid has a pKa of 4.4 in proteins. EAK16 has a calculated pI of 6.71. It was assumed that changes of pH would have a great effect on the β-sheet structure, especially when the charged groups are neutralized. However, CD spectra of EAK16 showed that pH had little effect on the secondary structure over a pH range of 1.5 to 11 (FIG. 10). The 3 mM stock solution of EAK16 was mixed with pH buffers at pH 1.5, 3, 7, and 11 to a final concentration of 10 µM and allowed to equilibrate for 4 hours before taking CD 10 measurements. Insignificant differences in ellipticity were observed at these pH. The pH profile showed a less than 10% decrease of $-[\theta]_{218\,nm}$ deg. cm²/decimole from pH 1.5 to 3, 7 and 11 (FIG. 10). However, when pH was increased beyond 12.5, precipitation of the peptide was observed.

Chemical denaturants. CD spectra measurements also showed that the β-sheet structure of EAK16 was not significantly affected by incubation in SDS (1% at 90° C.), 7M guanidine-HCl or 8M urea for over 16 hours. The peptide (3 mM stock) was mixed with water or different concentrations of guanidine-HCl or urea and allowed to incubate overnight before taking CD measurements. SDS was added to a peptide solution to a final concentration of 0.1% and incubated for 30 minutes. No significant differences in CD signals were observed even under the strongest denaturing conditions of 7M guanidine-HCl (FIG. 11) and 8M urea.

EXAMPLE 5

Identification, Cloning and Characterization of the Yeast Protein Zuotin

INTRODUCTION

DNA is capable of undergoing a number of conformational changes; the most dramatic of these is from right-handed B-DNA to left-handed Z-DNA. There are several conditions that are known to stabilize Z-DNA. For example, poly(dG-m⁵dC) converts readily to left-handed Z-DNA in vitro in the presence of millimolar concentrations of divalent metals and polyamines, as well as small peptides (Behe and Felsenfeld, 1981: Rich et al., 1984; Takeuchi et al., 1991). Certain DNA sequences, especially alternating purines and pyrimidines can adopt the Z-conformation in response to negative supercoiling (Peck et al., 1982). Inside the cell, negative supercoiling can be generated during transcription (Liu and Wang, 1987; Tsao et al., 1989). Furthermore, the equilibrium between B- and Z-DNA can be influenced by proteins that preferentially bind one of the two conformations (Lafer et al., 1985).

A number of studies suggests that Z-DNA may exist in viva (Jaworski et al., 1987; Rahmouni and Wells, 1989; Wittig et al., 1989); however, the extent of its occurrence is yet to be determined. Z-DNA has been implicated in some important biological processes, such as general DNA recombination (Bullock et al., 1986; Treco and Arnheim, 1986; Blaho and Wells, 1987; Wahls et al., 1990), and both positive and negative transcriptional regulation (Nordheim and Rich, 1983; Naylor and Clark, 1990).

RESULTS

Detection of a Poly(dG-m⁵dC) Binding Protein in *S. cerevisiae*

Two probes that can be stabilized in the Z-form were used to detect potential Z-DNA binding proteins. One is an ~600 bp fragment of ³²P-labelled poly(dG-m⁵dC) that is stabilized in the Z-DNA form by millimolar concentrations of $MgCl_2$ (Behe and Felsenfeld, 1981); the other is an oligonucleotide, [³²P] (dG-BR⁵dC)₂₂, that can be stabilized by millimolar concentrations of $MgCl_2$ or µM concentrations of $Co(NH_3)_6^{3+}$. Yeast whole cell extract, nuclear extracts, and phosphocellulose column fractions of yeast nuclear extracts were assayed by a gel retardation assay using either of these ³²P-labelled DNA fragments as a probe. The gel retardation assay was carried out with the probe in the presence of 10 mM $MgCl_2$ and a 400-fold excess of sheared salmon sperm B-DNA. Under these conditions, the polymer assumes the Z-DNA conformation. A Z-DNA-specific antibody was used for positive control. 1 µl of each fraction of yeast nuclear extract obtained by salt elution from the phosphocellulose column with 0.2–0.5M potassium phosphate (pH 7.4) was added to the assays.

A distinctive band shift was detected in assays of the phosphocellulose column fractions of yeast nuclear extracts. Both whole cell extracts and nuclear extracts produced a similar band shift. The nuclear extract fractions that did not bind to B-form DNA (Winter and Varshavsky, 1989) showed significant gel retardation using the probe [³²P]poly(dG-m⁵dC) in the Z-DNA form even in the presence of a 400-fold molar excess of sheared salmon sperm DNA. A similar band shift resulted from binding with polyclonal anti-Z-DNA antibody. The pooled fractions (FI) also showed binding activity to the oligonucleotide probe, [³²P] (dG-Br⁵dC)₂₂.

In order to determine if these band shifts were the result of authentic Z-DNA binding, negatively super-coiled plasmids of pUC19 and pUC19(GC) were used as competitor DNAs in gel retardation competition assays. In these assays, [³²P] (dG-Br⁵dC)₂₂ was incubated in the presence of a 2000-fold excess of sheared salmon sperm DNA with additions as follows: 1) no addition; 2) a monoclonal anti-Z-DNA antibody (mAb); 3) mAb plus additional 50 ng of negatively supercoiled plasmid pUC19 (without a Z-DNA insert); 4) mAb plus 25 ng of negatively supercoiled pUC19 (CG) (containing a Z-DNA segment); 5) fraction F1 yeast protein; 6) F1 plus additional 50 ng pUC19; and 7) F1 plus pUC19(GC). pUC19(GC) contains a 14 bp (dG-dC)₇ insert that can adopt the Z-conformation upon negative supercoiling. pUC19(GC) was assayed for its resistance to BssHII digestion (Vardimon and Rich, 1983; Azorin et al., 1984) to confirm the presence of the Z-DNA prior to the assay.

The results showed that monoclonal anti-Z-DNA antibody (Moller et al., 1982), used as a positive control, exhibited specific complex formation in the presence of the competing plasmid pUC19, but not in the presence of supercoiled plasmid pUC19(GC), which contains Z-DNA. Similar binding specificity was observed when a partially purified yeast fraction (FI) was used instead of the anti-Z-

DNA antibody. However, the complex observed with the protein fraction was more heterogeneous than that seen with the antibody. The Z-DNA binding activity of fraction FI was further purified using affinity chromatography to a poly(dG-m$^5$dC)-agarose column (FII) followed by Superose 12 (FIII) and Mono-S chromatography. The resultant active fraction (FIV) included a prominent 51 kDa protein that was still quite complex.

Identification of Zuotin by Southwestern Blotting

In order to identify the specific protein that interacts with the Z-DNA probe, a Southwestern blot was employed. Proteins in the Mono-S column fractions were transferred from a SDS-polyacrylamide gel to an Immobulon P membrane and exposed to conditions that favor renaturation. Subsequently, the filter was incubated in the presence of [$^{32}$P]poly(dG-m$^5$dC), stabilized in the Z-form by 15 mM MgCl$_2$ and a 300-fold excess of B-DNA (sheared salmon sperm DNA). An autoradiogram was made of the Southwestern blot and compared with a silver-stained gel of the Mono-S fractions.

The results showed that the poly(dG-m$^5$dC) probe bound a single polypeptide of ~51 kDa present in fractions 12 and 13, both of which were active in the band shift assay. There was also a weak signal in fraction 14. Although the fractions were quite complex, only the 51 kDa protein was detected by autoradiography. The putative Z-DNA binding protein was named zuotin (from the Chinese, zuo, meaning left).

Purification of Zuotin and Cloning of ZUO1

Approximately 5 μg of zuotin were gel-purified for amino acid composition analysis and N-terminal sequencing. The composition of hydrolyzed zuotin was obtained from the purified yeast protein and from the E. coli expressed or recombinant zuotin. Both were gel-purified and subjected to HCl hydrolysis, then, analyzed by HPLC with internal controls. The deduced composition of zuotin is derived from the DNA sequence of the open reading frame (ORF) of ZUO1. The amino acid composition of zuotin was 20.5% (Arg, Lys, and His), 18.5% (Glu and Asp), 14.1% (Thr, Ser, and Tyr) and 68.16% (Arg, Lys, Asp, Glu, Ser, Thr, Ala, and Leu). The amino acid composition of zuotin is shown in Table 4.

N-terminal sequencing yielded the following: MFSLPTLTSDI(E/D)V[EV](N)(H/S)(D), where [ ] and ( ) indicate moderate and low confidence assignments, respectively.

Degenerate 32mer oligonucleotides were designed by "reverse translation" of the N-terminal sequence. Alternative nucleotides were introduced at five positions in the oligonucleotide sequence. Nucleotides later determined to be mismatched are underlined. The oligonucleotides were used as a probe in Southern hybridization analysis of yeast genomic DNA. The Southern blot revealed a single hybridizing 2.4 Kb HindIII fragment. A yeast genomic EMBL3A library was subsequently screened and 14 clones isolated. Restriction mapping and Southern hybridization using the 32mer oligonucleotides revealed that one of the isolates contained a 2.4 Kb HindIII hybridizing fragment. This HindIII fragment was subcloned and the nucleotide sequence determined. The DNA sequence revealed an open reading frame (ORF), whose translated N-terminal sequence corresponded exactly to that of the N-terminal sequence determined from purified zuotin. To obtain the entire coding sequence of the ORF, a 3.1 Kb BamHI-EcoRI fragment was subcloned into the pBluescript vector (Stratagene), and the nucleotide sequence (Seq. ID #1) was determined by the dideoxy chain termination method. This sequence data is available from the EMBL sequence data bank under accession number X63612.

ZUO1 Encodes a 433 Residue Protein

The 3.1 Kb BamHI-EcoRI fragment contains the entire zuotin coding region (1291–2590), as well as 5' and 3' non-transcribed regions (SEQ ID NO: 1). There are tracts of alternating (AT)$_n$, A or T in the 5' nontranscribed region that could serve as regulatory sites. A homopurine/pyrimidine tract (with one exception) in the coding region that can adopt an alternative DNA conformation is present. The potential polyadenylation site at the 3' end of the gene is indicated. There is a long ORF encoding a 433 amino acid (aa) protein with a calculated molecular weight of 49 kDa. A second ORF in the same orientation within ZUO1 potentially encodes a 168 amino acid polypeptide. It remains to be seen if there is a translated product from this second reading frame. The 5' region of the 3.1 Kb fragment also has another ORF containing 210 codons, which encodes a yeast analogue of the E. coli biotin synthetase gene (bioB).

The 5' non-transcribed region of ZUO1 contains three A/T-rich segments and two alternating AT segments that may act as regulatory domains from transcription of the gene. There is also a purine-rich tract in the coding region that could adopt a DNA conformation different from conventional B-DNA (McCarthy and Heywood, 1987). The coding region comprises 1299 base pairs and the transcript of ZUO1 is ~1.7 Kb. ZUO1 is localized on yeast chromosome VII near ADE3.

Zuotin has several interesting features: it consists of 13% alanine, 20.6% positively charged residues (lysine, arginine and histidine) and 18.5% negatively charged residues (aspartic acid and glutamic acid) (Table 4). It has a pI of 8.8. The charged residues are clustered at the C-terminal end and there is one segment with 12 charged residues in a row (FIG. 1; + and − indicate positively and negatively charged amino acids, respectively). There are two continuous perfect and one imperfect octad tandem repeats of alternating alanine and charged amino acids (lysine and glutamic acid) in the alanine/lysine and arginine rich region (heavy underlining).

Zuotin also contains several potential phosphorylation sites, including sequences recognized by protein kinase C (●), casein kinase II (○), cAMP-dependent protein kinase (▼), and tyrosine kinase (★), as predicted by Prosite (FIG. 1) (Bairoch, 1991). There are also two potential CDC28 (or cdc2) phosphorylation sites (KTPFVRR from 21–27 and KTPIP from 201–205 of SEQ ID NO: 2 ⊗) (Moreno and Nurse, 1990). It has a bipartite nuclear targeting sequence: KKKAKEAAKAAKKKNKR from 340–356 of SEQ ID NO: 2 (wavy underlining; Robbins et al., 1991).

There are several regions that are predicted to form an α-helix (Chou and Fasman, 1978) and this includes the repeated octad segment (heavy underlining, FIG. 1). However, when a 16 residue peptide (EAK16) of the repeated segment was synthesized and examined by circular dichroism, a distinctive β-sheet structure was observed.

The zuotin protein is structurally similar to several known proteins. It shares a region of sequence similarity (residues 111–165) with DnaJ protein (SEQ ID NO: 8), which is involved in DNA replication of bacteriophages λ and P1 (Liberek et al., 1988) and with several other yeast proteins: YDJ1 (SEQ ID NO: 12; Caplan and Douglas, 1991), SIS1 (SEQ ID NO: 11; Luke et al., 1991), SCJ1 (SEQ ID NO: 9; Blumberg and Silver, 1991) and SEC63 (or NPL1) (SEQ ID NO: 14; Sadler et al., 1989). All of these proteins include the hexapeptide motif, KYHPDK. This hexapeptide motif is also present in both the small t and large T antigens of avian budgerigar fledgling disease virus (SEQ ID NO: 13; Rott et al., 1988) and in the csp29 and csp32 proteins expressed in the retina and brain of Drosophila (SEQ ID NO: 10; Zinsmaier et al., 1990). The consensus sequence shown in SEQ ID NO: 28 was obtained by computer analysis using the GeneWorks version 2.0 (1991) program.

There is also sequence similarity between another region of zuotin (residues 300–363) and several histone H1 variants, including human H1a, H1b and H1c, chicken H1.11L and H1.11R (SEQ ID NO: 17), and sea urchin H1β and H1δ (SEQ ID NO: 16). The conserved region is in the extended C-terminal tail of histone H1, a region rich in alanine, lysine and arginine residues. For example, the sequences from 300–363 in zuotin and 146–205 in sea urchin histone H1 (SEQ ID NO: 16) are 64% similar and 46% identical.

The DnaJ similar region is located from amino acids 111 to 165 and the histone HI similar region is located from amino acids 300 to 363 of zuotin.

Construction and Analysis of zuo1 Mutants

Figure 2:
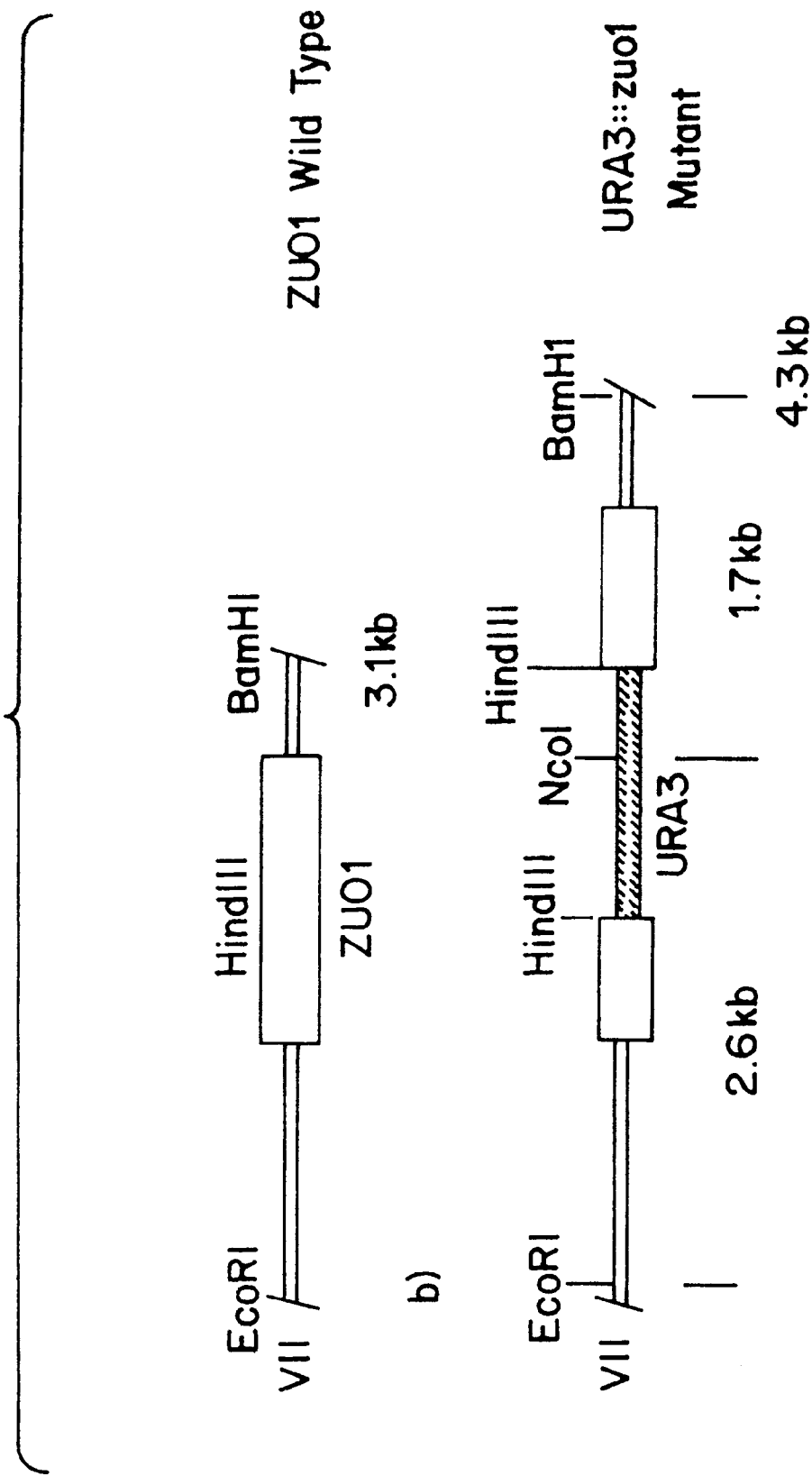
FIG. 2 is a restriction map of the wild type ZUO1 locus and the URA3::zuo1 disrupted locus.
Figure 3A:
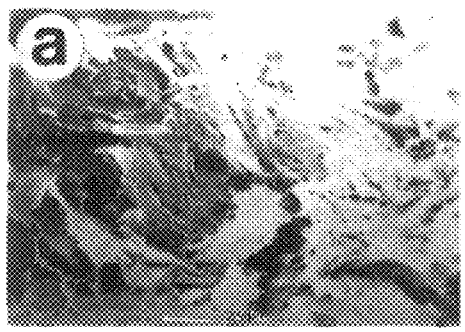
FIGS. 3a, 3b, 3c, 3d, 3e, 3f, 3g and 3h are serial photographs of membranes under scanning electron microscopy (SEM).
Figure 3E:
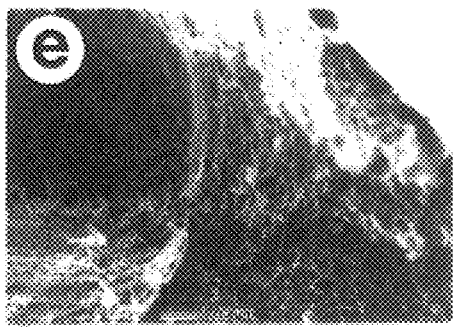
Figure 3B:
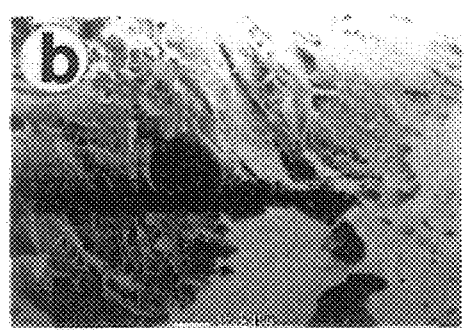
Figure 3F:
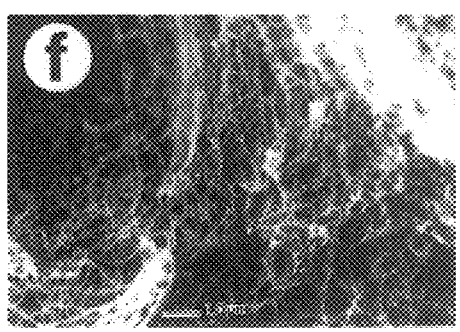
Figure 3C:
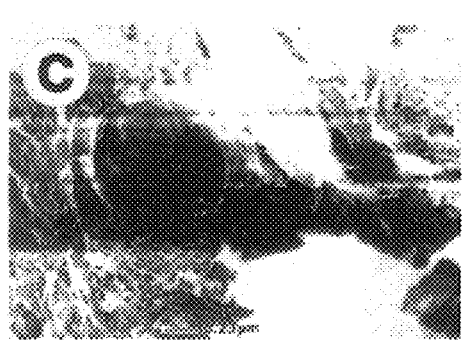
Figure 3G:
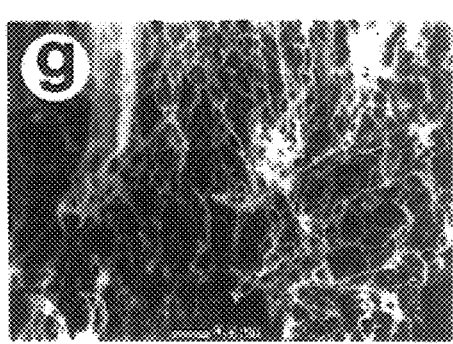
Figure 3D:
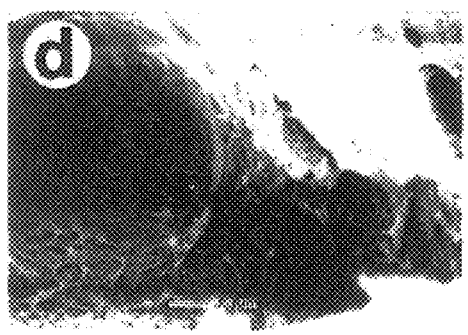
Figure 3H:
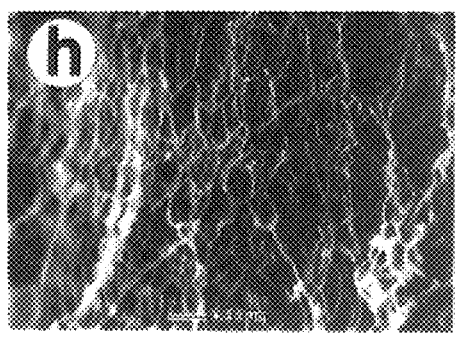

In order to generate an interrupted zuo1 allele, the 1.2 Kb HindIII fragment containing the *S. cerevisiae* URA3 gene was inserted at a unique HindIII site of the ZUO1 coding region (FIG. 2). Wild type DNA has a 3.1 Kb EcoRI-BamHI fragment, whereas, the disrupted mutant has a 4.3 Kb fragment. The plasmid pZUO1::URA3 was then linearized and used to transform DM27, a diploid ura3 yeast strain. Diploid Ura+ transformants, expected to be heterozygous at the ZUO1 locus, were selected and confirmed to harbor disruption at the ZUO1 locus. The heterozygous diploid strains were subsequently sporulated and subjected to tetrad analysis. Tetrads yielded four viable colonies: two large and two small colonies, in which Ura+ phenotypes co-segregated with the small colonies (i.e., a slow growth phenotype). Southern blot analysis using DNA from four tetrads revealed that all clones with the slow growth phenotype harbor the 1.2 Kb insertion. The results showed that the insertion of URA3 at the ZUO1 locus produces a similar slow growth phenotype.

Expression of ZUO1 in *E. coli*

In order to verify that the cloned *S. cerevisiae* ZUO1 gene encodes the putative Z-DNA binding protein, ZUO1 was expressed in *E. coli* using a T7 expression system (Studier et al., 1990). ZUO1 was cloned in pET8c at the unique NcoI and BamHI sites. When the lacUV5 promoter was induced with IPTG, a protein band with an apparent molecular weight of ~51 kDa was detected. This protein was not seen in the cell extract from pET8C transformants induced with IPTG nor in the cell extract from uninduced pETZUO transformants. Analysis of the protein composition and the N-terminal sequence of the purified and the *E. coli* expressed or recombinant zuotin are essentially the same, indicating that zuotin was expressed correctly.

In attempting to purify zuotin expressed in *E. coli*, Applicants found that the recombinant zuotin was sequestered in inclusion bodies. However, enough material was in solution so that crude cell extracts and partially purified zuotin could be prepared and assayed by the band shift assay. Recombinant zuotin was partially purified by chromatography of crude cell extract from induced pETZU01 transformants through phosphocellulose. $^{32}$P-labelled poly(dG-m$^5$dC) in the Z-form was incubated with the crude cell extract or with partially purified zuotin in the presence of sheared salmon sperm DNA, poly(dG-dC), or poly(dG-Br$^5$dC). Assays were run on: 1) labelled probe alone; 2) crude cell extract from induced pET8c transformants; 3) crude cell extract from uninduced pETZUO1 transformants; 4) crude cell extract from induced pETZUO1 transformants; 5) partially purified recombinant zuotin; 6) partially purified yeast zuotin; 7)–10) partially purified recombinant zuotin with 20-, 40-, 100-, and 200-fold excess of salmon sperm DNA; 11)–12) partially purified recombinant zuotin with 20- and 40-fold excess of poly(dG-dC); 13)–14) partially purified recombinant zuotin with 20- and 40-fold excess of poly(dG-Br$^5$dC); 15)–17) partially purified yeast zuotin with 20-, 40-, and 200-fold excess of salmon sperm DNA; 18) partially purified yeast zuotin with 40-fold excess of poly(dG-dC); 19) partially purified yeast zuotin with 40-fold excess of poly (dG-Br$^5$dC); and 20) an anti-Z-antibody (as control).

These gel shift assays showed that partial purification through phosphocellulose yielded a fraction with Z-DNA binding ability. The strongly shifted band bound to labelled poly(dG-m$^5$dC) even in the presence of a 40-fold excess of salmon sperm DNA. On adding a 40-fold excess of poly (dG-dC), which can form Z-DNA under certain conditions, a somewhat weaker band was visible. Similar results were found with zuotin isolated from yeast. It is interesting that the band shift with yeast zuotin migrated slightly further towards the positive side of the gel than the bacterially expressed zuotin. It is possible that this difference could be due to differences in phosphorylation or other post-translational modifications that were not carried out in *E. coli*. Furthermore, the yeast zuotin bound Z-DNA more tightly than the bacterially expressed zuotin. It is known, for example, that phosphorylation modifies the DNA binding activity of the yeast centromere binding protein CBF3 (Lechner and Carbon, 1991). Analysis of the zuotin sequence using the Prosite computer program (Bairoch, 1991) suggests that zuotin may be phosphorylated. Attempts are now being made to express zuotin in other systems, including those which phosphorylate proteins.

DNA Binding Properties of Zuotin

Yeast protein fractions containing zuotin are able to bind both poly(dG-m$^5$dC) and oligo(dG-BR$^5$dC)$_{22}$ in the Z-form as well as negatively supercoiled pUC19(GC) containing a Z-form segment in the presence of competitor B-DNA. Since zuotin has not been purified to homogeneity, it is difficult to obtain a precise Z-DNA binding constant. The yeast zuotin is estimated to have a several hundred-fold enhanced affinity for Z-DNA relative to B-DNA under the experimental conditions used, while the *E. coli* expressed zuotin binds less tightly. It would not be surprising if proteins which interact with Z-DNA have binding motifs different from the binding motifs of several proteins known to interact with B-DNA. B-DNA has distinct major and minor grooves, and B-DNA binding proteins tend to either anchor their binding motifs in the major grooves or lie along the minor grooves (reviewed in Seeman et al., 1976; Pabo and Sauer, 1984; Churchill and Travers, 1991). Such binding to B-DNA is relatively tight and, in some cases, very specific. On the other hand, Z-DNA does not have a distinct major groove nor a highly accessible minor groove. Thus, it is possible that a Z-DNA binding protein would not be able to anchor its binding motif to the region corresponding to the major groove. It is possible that the binding constants of Z-DNA binding proteins are lower than those of B-DNA proteins. It has been shown that many DNA sequences can adopt the left-handed Z-conformation (Rich et al., 1984). Thus, proteins that recognize Z-DNA may be conformationally specific as well as sequence specific.

The binding of both yeast zuotin and bacterially expressed zuotin to poly(dG-m$^5$dC) cannot be competed by 40-fold excess of poly(dG-dC), 200-fold excess of poly(dA-dT), nor several thousand-fold of salmon sperm DNA. However, a mere 4-fold excess of poly(dG-Br$^5$dC) in the Z-form completely inhibits zuotin binding to the probe. These results suggest that zuotin may recognize the conformation of DNA rather than specific sequences per se. Another example of a protein that recognizes DNA conformation specifically is HMG1 (high mobility group protein). HMG1 and proteins containing HMG1 domains bind DNA not by its sequence but rather by the DNA conformation at the crossing of two duplexes (Bianchi et al., 1992; Lilley, 1992).

The Biological Function of Zuotin

Previous studies have suggested that potential Z-forming sequences, i.e., (GC/GC)n, (GT/AC)n and other alternating purine/pyrimidine segments, exist in the intergenic regions of many organisms, including those of yeast (Hamada et al., 1982). The GT/AC segments have been implicated in inducing homologous DNA recombination in vivo (Bullock et al., 1986; Treco and Arnheim, 1986; Wahls et al., 1990). Also, a DNA strand transferase from human cells has been partially purified using a Z-DNA affinity column (Fishel et al., 1988). Recently, it has been shown that specific alternating purine/pyrimidine segments in the upstream region of c-myc form Z-DNA during active transcription.

The precise biological function of zuotin is not known at the present time. Since zuotin appears to be of nuclear origin, binds to DNA, is relatively abundant and may potentially be phosphorylated by protein kinases and dephosphorylated by phosphatases during the cell cycle, it could be involved in chromosome organization. The threonine within the KTPFVRR and KTPIP sequences may be phosphorylated by the S. cerevisiae CDC28-CLN complex during the cell cycle.

Computer sequence comparison analysis revealed that two different regions of zuotin have similarities with known proteins. The first region of zuotin (residues 111–165) has 46% identity and an overall 70% similarity with the N-terminus of E. coli DnaJ protein (residues 16–67) (SEQ ID NO: 8). The DnaJ protein is a heat shock protein involved in protein folding; it is also active in phage λ and P1 replication in vivo and in vitro through its interaction with DnaB helicase (Liberek et al., 1988; Zylicz et al., 1989). This region of zuotin also shares similarity with several other yeast proteins: YDJ1 (a yeast DnaJ homolog), which may be involved in protein assembly into the endoplasmic reticulum and nucleus (SEQ ID NO: 12; Caplan and Douglas, 1991); SCJ1, which is involved in protein sorting (SEQ ID NO: 9; Blumberg and Silver, 1991); and SIS1, which is an essential protein and may be involved in yeast DNA replication by mediating a specific protein-protein interaction (SEQ ID NO: 11; Luke et al., 1991). Similarity was also found to the yeast protein SEC63 (or NLS1), which is important for protein assembly into the endoplasmic reticulum and the nucleus (SEQ ID NO: 14; Sadler et al., 1989). Both YDJ1 and SIS1 have several cysteines that could potentially form a zinc finger DNA binding motif, but zuotin has only one cysteine and no zinc finger motif could be found. All the above proteins have a conserved hexapeptide, KYHPDK, except SEC63, in which F has replaced Y. This peptide motif may play an essential role in these diverse proteins. Moreover, both small t and large T antigens (SEQ ID NO: 13) of the avian polyomavirus, budgerigar fledgling disease virus, as well as the csp29 and csp32 (SEQ ID NO: 10) proteins expressed in Drosophila retina and brain have this identical hexapeptide motif (Zinsmaier et al., 1990). Recently, a human nuclear protein HDJ-1 has also been shown to be similar at both the N- and C-termini to the DnaJ protein (SEQ ID NO: 15; Raabe and Manley, 1991).

A second region of similarity in zuotin (residues 300–363) is related to histone H1 and some of its variants, such as human H1a, H1b and H1c, chicken H1.11L and H1.11R (SEQ ID NO: 17), and sea urchin H1β and H1δ (SEQ ID NO: 16). It is significant that histones H2A, H2B, H3 and H4 do not have regions similar to zuotin. Calf thymus histone H1 has been shown to have a higher affinity to Z-DNA than to B-DNA and it is able to convert Z-DNA to B-DNA, a transition that can be measured using circular dichroism spectroscopy (Russell et al., 1983; Mura and Stollar, 1984). Also, the Drosophila histone H1 has been previously purified using a Z-DNA affinity column and Z-DNA binding assays. It is possible that zuotin has some elements of histone H1-related activity in yeast.

A subportion of this histone-like region from amino acids 306 to 339 (heavily underlined in FIG. 1) is a likely candidate for a DNA-binding domain. In related studies, Applicants found that the peptides KAKAK (SEQ ID NO: 29) and KAK were able to bind to B-DNA and convert it to the Z conformation. Amino acid substitutions at the middle lysine of KAKAK (SEQ ID NO: 30) resulted in a loss of activity, but changes at the carboxyl-terminal K did not significantly affect activity. A peptide, KAHAK, was active in converting B-DNA to Z-DNA only when the histidine was protonated (at low pH). The KAKAX motif (SEQ ID NO: 31) (where X is variable) occurs twice in the 306–339 region and also occurs in the peptide, EAK16. These observations are consistent with the structural similarity of this region to histone H1.

In an attempt to see whether zuotin is found in other organisms, a Southern "zooblot" was carried out in which various DNAs were probed with zuotin DNA. Of 12 plant and animal species that were probed under low stringency, all were negative except yeast. This suggests that zuotin is a yeast-specific protein.

Mutant yeast cells in which ZUO1 was disrupted exhibit a slow growth phenotype. Thus, the function of ZUo1 appears not to be essential, rather it may be involved in some activity that is needed to maintain rapid cell growth.

Materials and Methods

Yeast Strains and Media

The genotype and sources of yeast S. cerevisiae used in this work are as follows: DB2670, MATα, his3-Δ200, ura3-52, can 1, pep4::HIS3, prbl-Δ1.6R was obtained from D. Botstein; 20B-12, MATα, pep4-3, txp1 has been previously described (Jones, 1977); DM27, MATα/α, his3/HIS3, leu2/LEU2, ade2/ADE2 ura3/ura3, trp1/trp1, cyh/CYH was obtained from D. Dawson. Cells were grown in YPD medium (1% yeast extract, 2% bactopeptone and 2% glucose). SD medium contained 0.6% Difco yeast nitrogen base without amino acids and 2% glucose. Nutrients essential for auxotropic strains were supplied at concentrations recommended by Sherman et al. (1986). The plasmid, pUC19(GC), was obtained from B. Johnston. Characterization of the anti-Z-DNA Z-22 monoclonal antibody and polyclonal goat anti-Z-DNA antibody have been described (Moller et al., 1982).

Preparation of the Poly(dG-m$^5$dC) Affinity Matrix

Poly(dG-m$^5$dC) DNA (Pharmacia) (1.6 mg in 3 ml) was digested to an average size of ~600 bp using DNase I in 50 mM Tris-HCl (pH 7.5), 30 μg/ml BSA in the presence of 2 mM MnCl$_2$ to produce blunt ends (Maniatis et al., 1982). The digested DNA was deproteinized and resuspended in T4 DNA polymerase buffer in the absence of dNTP and incubated with T4 DNA polymerase at 10° C. for 10 minutes. Subsequently dGTP and biotinylated dCTP (ENZO) were added to 1 mM final concentration, and incubation was continued at 37° C. for 2 hours. DNA was then separated from unincorporated nucleotides by phenol and chloroform extraction, followed by two ethanol precipitations. Then, DNA was dissolved in 0.1M NaCl, 1 mM EDTA, 10 mM Tris-HCl (pH 7.5) and incubated with 1 ml of streptavidin-agarose (BRL) overnight by gentle inversion. Under these conditions, more than 60% of the input DNA was bound to streptavidin-agarose as determined by $A_{260}$ measurement after pelleting the agarose. The DNA matrix was then washed extensively with 40 column volumes of buffer (10 mM Tris-HCl, pH.7.5, 50 mM KCl and 15 mM $MgCl_2$). The column wash was assayed for unbound DNA (using the BluGene non-radioactive nucleic acid detection system, BRL) to assess the column stability.

Purification and Sequencing of Zuotin

The preparation of crude nuclear fractions has been described previously (Winter and Varshavsky, 1989). Crude total cell extract (from strain DB2670) was prepared from mid-log phase yeast cells (18 L at ~2.4×10$^7$ cells/ml). Yeast cells were collected at 4500×g for 10 minutes at 4° C. and washed twice with water. The cell pellet was resuspended in 600 ml of 0.2M potassium phosphate (pH 7.5), 5 mM EDTA, 1 mM phenylmethylsulfonyl fluoride (PMSF), 0.8 μg/ml pepstatin A and 10% glycerol. The final volume was ~800 ml. The cell suspension was processed through a high pressure compressor at 900 psi ~50 passages to break the cells. The suspension was then centrifuged at 12,000×g for 10 minutes at 4° C. The supernatant (~720 ml) was frozen at −80° C. Fractionation of whole cell extract on a phosphocellulose P-II column and on a Mono-S column were as described by Winter and varshavsky (1989). The pooled fraction (FI) containing binding activity to poly(dG-m$^5$dC) in the presence of sheared salmon sperm DNA was diluted 6-fold to achieve a potassium phosphate concentration of ~50 mM (420 ml). $MgCl_2$ was then added to a final concentration of 15 mM for loading on the poly(dG-m$^5$dC) affinity column. The column was washed with 10 volumes of the column buffer and eluted with a linear gradient of 25 ml 0.1–1.0M KCl without $MgCl_2$ (FII).

The eluted proteins were then loaded on a Superose-12 gel filtration column. One ml fractions were collected and assayed for the Z-DNA binding activity (FIII). These fractions were pooled, diluted 3-fold and loaded on a Mono-S column. The Mono-S column was washed extensively and eluted with a linear 47 ml gradient of buffer, 0–1.0M NaCl, in 10 mM sodium phosphate (pH 7.2). The 1 ml fractions containing Z-DNA binding activity (FIV) were analysed by SDS-PAGE.

For protein composition and sequence analysis, the pooled Mono-S column fractions 12 and 13 were resolved on a 9% polyacrylamide-SDS gel. After electrophoresis, the protein was electroblotted on Immobulon (Millipore), briefly stained with Coomassie Blue and washed. The band with an apparent molecular weight of 50 kDA was excised and ¼ of the sample was used for amino acid composition analysis. The remaining sample was N-terminal sequenced by automated Edman degradation in an Applied Biosystems 470A Protein Sequencer equipped with on-line 120A PTH analyser.

Band Shift and Competition Experiments

A gel retardation assay was employed to detect proteins with affinity to left-handed Z-DNA. In these assays, two kinds of left-handed DNA probes were used. One was poly(dG-m$^5$dC) (Pharmacia) stabilized in the left-handed Z-form by 15 mM $MgCl_2$. The DNA probe was made as follows: DNA polymer was digested with DNase I in the presence of 2 mM $MnCl_2$ and fragment of ~600–1000 bp were gel purified and labelled with T4 DNA polymerase in the presence of dCTP and [α-$^{32}$P]dGTP (3000 Ci/mM) (Maniatis et al., 1982). The other probe was derived from a synthetic 44mer oligo(dG-Br$^5$dC)$_{22}$, labelled using Klenow polymerase with [α-$^{32}$P]dGTP, and stabilized in the Z-DNA conformation by 10 mM $MgCl_2$, or 0.1 mM Co(NH$_3$)$_6^{3+}$. In the assay reaction, 2 μl of diluted fraction samples were incubated for 20 minutes at room temperature in 20 μl of 50 mM Tris-HCl (pH 8.0), 15 mM $MgCl_2$, 5% sucrose, 0.1% Triton X-100, 10 mM β-mercaptoethanol, a 2000-fold excess of sheared salmon sperm DNA, and the labelled Z-DNA probe. In the competition assays, supercoiled pUC19 and pUC19(CG) were added to the reaction samples separately. The samples were then electrophoresed in 1.5% agarose for poly(dG-m$^5$dC) (10 mM $MgCl_2$, 1× TBE, pH 8.4) or 4% polyacrylamide for (dG-Br$^5$dC)$_{22}$ (1× TBE, pH 8.4). After electrophoresis, the gel was dried and exposed to X-ray film.

Southwestern Blotting

Mono-S column fractions containing proteins were electrophoresed on 9% polyacrylamide-SDS gel, as described by Laemmli (1970). After electrophoresis, the gel was soaked in the running buffer without SDS but with 20% methanol at room temperature for 45 minutes with agitation. The proteins were then blotted onto two sheets of Immobulon P membrane (Millipore) at 1.5 mA/cm$^2$ at room temperature for 60 minutes. After transfer, the membrane was washed once with 5% milk powder, 30 mM HEPES (pH 7.4) (Celenza and Carlson, 1986); then, washed three times (3 minutes each) with 10 mM Tris-HCl, 50 mM NaCl, 1 mM EDTA, 10 mM $MgCl_2$ (STEM). After washing, the membrane was incubated with 15 ml of the above buffer containing 10 μg/ml sheared salmon sperm DNA. A DNA probe (average size 1300 bp) (at 2.55×10$^6$ c.p.m./ml of poly(dG-m$^5$dC)) was added to a final concentration of 30 ng/ml and the incubation continued for 1 hour at room temperature with gentle agitation (50 r.p.m.). In this buffer with 10 mM MgCl$_2$, the polymer is in Z-DNA conformation (Behe and Felsenfield, 1981). The membrane was then washed four times (8 minutes each) with STEM at room temperature. The membrane was air-dried and exposed to X-ray film.

Cloning and Sequencing of ZUO1

The first 11 amino acids of the N-terminal sequence of zuotin (MFSLPTLTDI) were used to design oligonucleotides, with yeast codon usage as a guideline (Sharp et al., 1986). The pools contained an equal molar mixture of 64 different 32mer sequences as follows:

```
                                           (SEQ ID NO: 22)
5'-ATGTTTTCTTTGCCAACTTTGACTTCTGATAT-3'
          C    T C    C     C
```

These oligonucleotides were gel-purified and labelled using [γ-$^{32}$P]ATP and T4 polynucleotide kinase to a specific activity 200–500 μCi/μg. The labelled oligonucleotides were first used in genomic Southern blot hybridization to determine optimal conditions for screening a phage λ library of yeast DNA. For this, yeast DNA was digested with HindIII, separated on an 1% agarose gel and blotted onto a Gene Screen filter (New England Nuclear). The filter was hybridized at 40° C. in 4.5% SDS, 0.34M NaCl, 1 mM Na-EDTA, 10 mg/ml BSA and 0.16M sodium phosphate buffer (pH 7.0) overnight. The filters were then washed at temperatures between 40 and 80° C. with washing steps at 5° C. in 3M tetramethyl-ammonium chloride, 2 mM EDTA, 0.1% SDS, and 50 mM Tris-HCl (pH 8.0), as described by Wood et al. (1985). At the washing temperature of 65° C., there was a single hybridization band of ~2.4 Kb. This temperature was chosen for screening a S. cerevisiae genomic phage γ EMBL3A DNA library. Screening of the phage EMBL3A library was essentially the same as described by Winter and Varshavsky (1989). Thirteen positive phage plaques were isolated. Phage DNAs from 11 clones were purified from the confluent plate lysates. The DNA was then digested with several restriction enzymes and a Southern blot was performed, as described previously. The restriction pattern and hybridization analysis revealed that the clones fell into three classes. One phage clone with a 3.1 Kb EcoRI and BamHI fragment was chosen for subcloning into pBluescript. Sequence analysis was carried out as described by Sanger et al. (1977). The 3.1 Kb DNA fragment was sequenced on both strands with synthetic oligonucleotides as primers using the USB Sequenase kit (Version 2.0).

Expression of Zuotin in E. coli

Zuotin was expressed in E. coli using the T7 pET expression system (Studier et al., 1990). In order to insert ZUO1 into the NcoI site of the pET8c vector, two bases flanking the initiation ATG were modified: at −1 (GC) and at +4 (TG). This produced an amino acid change immediately after Met of (Phe→Val). An oligonucleotide of 25 bases, CAAGAG-TAACCATGGTTTCTTTACC (SEQ ID NO 18), was synthesized and used as a primer for PCR amplification. A fragment of 1.8 Kb containing the entire coding region of zuotin was amplified by polymerase chain reaction (PCR) from pSKIIZUO1 and ligated into pET8c which was previously digested with NcoI and BamHI and dephosphorylated.

The pETZUO1 clones were isolated by colony hybridization using the coding region of ZUO1 as a probe. Extensive restriction mapping and sequencing using the T7 primer and several internal primers confirmed the correct in-frame cloning of ZUO1. Furthermore, the zuotin expressed in E. coli had its N-terminal region sequenced and its composition analysed by hydrolysis in order to confirm expression of the correct protein (Table 4).

E. coli strain, BL21E3LysS, which carries T7 RNA polymerase in the chromosome of the host under the control of the lacUV5 promoter, was transformed with pETZUO1. The transformants were induced with 0.5 mM IPTG after the cells had reached a density of 0.5 O.D. ($A_{600}$). Cells were harvested 3 hours after induction, lysed, treated and analysed as described by Sambrook et al. (1989).

After cells were lysed by sonication, the cell suspension was centrifuged at 8000×g for 20 minutes at 4° C., and both supernatant and pellet were saved. The pellet was resuspended in buffer containing 10 mM Tris-HCl, 50 mM NaCl and 1 mM PMSF, and then urea was added to a final concentration of 4M in order to denature the inclusion bodies. The suspension was stirred at 4° C. for 4 hours. The suspension was then dialysed overnight at 4° C. with three changes of buffer. The dialysed suspension was centrifuged at 10,000×g for 30 minutes. The supernatant was then loaded on the phosphocellulose column. The column was washed in 100 mM $KH_2PO_4$ buffer and eluted with 1.0M KH2PO$_4$. The eluent was dialyzed and used for characterization.

Construction of zuo1 Disruption Mutants

The gene disruption method of Rothstein (1983) was used for generating the zuo1 mutants in the yeast genome. A 1.17 Kb HindIII fragment containing URA3 was inserted at the unique HindIII site within the coding region of ZUO1 (corresponding to amino acid position 186). The DNA was then cut with EcoRI and BamHI, and the released fragment was used to transform a diploid S. cerevisiae DM27. Standard techniques were used for yeast transformation, sporulation and tetrad dissection (Sherman et al., 1986). Both orientations of the URA3 insert were used and yielded the same results.

Computer Analysis of Zuotin

The predicted structure of zuotin was analysed by computer algorithms using Pepplot, FastA, BLAST and others, in the Genetics Computer Group (GCG) package, as installed at the Whitaker College Computer Facility at the Massachusetts Institute. of Technology. GeneWorks Version 2.0 (1991, Intelligenetics, Inc., Mountain View) was used for zuotin alignment with DnaJ and other proteins.

TABLE 1

| Peptide | Sequence[a] | DMEM[b] | PBS | Water | Structure[c] |
|---|---|---|---|---|---|
| EAK16 | Ac—HN—AEAEAKAKAEAEAKAK—CONH$_2$ | ++++ | ++++ | − | β |
| EAK12 | Ac—HN—AEAKAEAEAKAK—CONH$_2$ | ++ | + | − | α, β |
| EAK8 | H$_2$N—AEAEAKAK—COOH | − | − | − | RC |
| RAD16 | H$_2$N—ARARADADARARADAD—COOH | ++++ | ++++ | − | ND |
| ARD8 | H$_2$N—ARARADAD—COOH | − | − | − | ND |
| β-Amyloid (1–28) | H$_2$N—DAEFRHDSGYEV—HHQKLVFFAEDVGSNK—COOH | − | − | − | RC, α, β |
| β-Amyloid (25–35) | H$_2$N—GSNKGAIIGLM—CONH$_2$ | − | − | − | ND |
| Substance P | H$_2$N—RPKQQFGLM—COHN2 | − | − | − | ND |
| Spantide | H$_2$N—(D)RPKPQQ(D)WL(D)L—CONH$_2$ | − | − | − | ND |

[a]One letter amino acid code is used.
(D) in Spantide is a D amino acid incorporated into the peptide.
[b]The + and − denotes the presence and absence of the membranous structure, respectively.
[c]α, α-helix. β, β-sheet. RC, random coil. ND, not determined
(EAK16 is 310–325 of SEQ ID NO: 2. EAK12 is SEQ ID NO: 24. EAK8 is 310–317 of SEQ ID NO: 2. RAD16 is SEQ ID NO: 3, ARD8 is 1–8 of SEQ ID NO: 3. β-Amyloid (1–28) is SEQ ID NO: 4. β-Amyloid (25–35) is SEQ ID NO: 5. Substance P is SEQ ID NO: 6. Spantide is SEQ ID NO: 7.)

TABLE 2

| | Potential membrane-forming peptides | |
|---|---|---|
| Name | Sequence (N→C) | |
| KAE16 | AKAKAEAEAKAKAEAE | (SEQ ID NO: 32) |
| AKE16 | AKAEAKAEAKAEAKAE | (SEQ ID NO: 33) |
| EKA16 | EAKAEAKAEAKAEAKA | (SEQ ID NO: 34) |
| KEA16 | KAEAKAEAKAEAKAEA | (SEQ ID NO: 35) |
| AEK16 | AEAKAEAKAEAKAEAK | (SEQ ID NO: 36) |
| DAR16 | ADADARARADADARAR | (SEQ ID NO: 37) |
| RAD16 | ARADARADARADARAD | (SEQ ID NO: 38) |
| DRA16 | DARADARADARADARA | (SEQ ID NO: 39) |
| RDA16 | RADARADAAADARADA | (SEQ ID NO: 40) |
| ADR16 | ADARADARADARADAR | (SEQ ID NO: 41) |
| ARDAKE16 | ARADAAAEARADAKAE | (SEQ ID NO: 42) |
| AKEARD16 | AKAEARADAKAEARAD | (SEQ ID NO: 43) |
| ARKADE16 | ARAKADAEARAKADAE | (SEQ ID NO: 44) |
| AKRAED16 | AKKAAEADAKARADAE | (SEQ ID NO: 45) |
| AQ16 | AQAQAQAQAQAQAQAQ | (SEQ ID NO: 46) |
| VQ16 | VQVQVQVQVQVQVQVQ | (SEQ ID NO: 47) |
| YQ16 | YQYQYQYQYQYQYQYQ | (SEQ ID NO: 48) |
| HQ16 | HQHQHQHQHQHQHQHQ | (SEQ ID NO: 49) |
| AN16 | ANANANANANANANAN | (SEQ ID NO: 50) |

TABLE 2-continued

Potential membrane-forming peptides

| Name | Sequence (N→C) | |
|---|---|---|
| VN16 | VNVNVNVNVNVNVNVN | (SEQ ID NO: 51) |
| YN16 | YNYNYNYNYNYNYNYN | (SEQ ID NO: 52) |
| HN16 | HNHNHNHNHNHNHNHN | (SEQ ID NO: 53) |
| ANQ16 | ANAQANAQANAQANAQ | (SEQ ID NO: 54) |
| AQN16 | AQANAQANAQANAQAN | (SEQ ID NO: 55) |
| VNQ16 | VNVQVNVQVNVQVNVQ | (SEQ ID NO: 56) |
| VQN16 | VQVNVQVNVQVNVQVN | (SEQ ID NO: 57) |
| YNQ16 | YNYQYNYQYNYQYNYQ | (SEQ ID NO: 58) |
| YQN16 | YQYNYQYNYQYNYQYN | (SEQ ID NO: 59) |
| HNQ16 | HNHQHNHQHNHQHNHQ | (SEQ ID NO: 60) |
| HQN16 | HQHNHQHNHQHNHQHN | (SEQ ID NO: 61) |
| AKQD18 | AKAQADAKAQADAKAQAD | (SEQ ID NO: 19) |
| VKQ18 | VKVQVDVKVQVDVKVQVD | (SEQ ID NO: 62) |
| YKQ18 | YKYQYDYKYQYDYKYQYD | (SEQ ID NO: 63) |
| HKQ18 | HKHQHDHKHQHDHKHQHD | (SEQ ID NO: 64) |

TABLE 3

Optical properties of EAK16 at different temperature

| Temp (° C.) | $\lambda_1$ 218 nm | $-[\theta_1]$ X1,000 | $\lambda_2$ 195 nm | $[\theta_2]$ X1,000 | Ratio $[\theta_2]/[\theta_1]$ |
|---|---|---|---|---|---|
| 25 | | 16 | | 62 | 3.9 |
| 37 | | 15 | | 60 | 4.0 |
| 55 | | 14 | | 55 | 3.9 |
| 70 | | 13 | | 54 | 4.1 |
| 90 | | 12.5 | | 50 | 4.0 |

TABLE 4

Amino acid composition analysis of zuotin

| | Hydrolysis | | Deduced from |
|---|---|---|---|
| | E. coli (%) | Yeast | DNA (%) |
| Arg | 5.7 | 7.6 | 6.0 |
| Lys | 9.2 | 11.9 | 12.9 |
| His | 3.1 | 1.4 | 1.6 |
| Glu | (11.5) | (12.1) | 9.7 |
| Gln | | | 2.3 |
| Asp | (11.0) | (11.5) | 8.8 |
| Asn | | | 3.2 |
| Ser | 7.0 | 7.4 | 6.9 |
| Thr | 4.4 | 5.0 | 5.1 |
| Tyr | 2.4 | 1.8 | 2.1 |
| Ala | 11.2 | 13.0 | 12.9 |
| Val | 6.3 | 4.8 | 5.5 |
| Leu | 6.8 | 6.6 | 5.8 |
| Ile | 3.6 | 3.0 | 3.2 |
| Phe | 3.8 | 4.5 | 5.1 |
| Trp | 0.0 | 0.0 | 1.4 |
| Pro | 4.0 | 3.2 | 3.5 |
| Gly | 5.0 | 6.1 | 3.0 |
| Met | 0.7 | 0.1 | 0.7 |
| Cys | 0.0 | 0.0 | 0.2 |

The numbers in parentheses are combined percentages of Glu/Gln and Asp/Asn as they are individually indistinguishable in the hydrolytic analysis.

EXAMPLE 6

In Vitro Cell Attachment and Growth

The suitability of these materials for supporting in vitro cell attachment and growth was tested by introducing a variety of cultured cells to membranes formed by EAK16, RAD16, heteropolymers of EAK16 and RAD16 and RADA16. Cultured cells formed stable attachments and proliferated on the biomaterials. The biomaterials containing the RAD sequence provided a better support for the cell types tested (Tables 5–7).

3T3 fibroblast cells were introduced to membranes of RAD16 and EAK16 in normal serum-containing medium or in serum-free medium containing 30 μg/ml cyclohexamide (cells used for this condition were pretreated in this medium for 2 hours before plating). Cells were allowed to attach to the membranes for 30 minutes, 1 and 8 hours at 37° C. The attached cells were shaken for 10 minutes on a rotary rocker at 60 r.p.m., then scored under phase contrast microscopy. The decrease in cells attached to the membrane in the serum-free condition reflects cell loss due to serum deprivation. Similar decreases in cells were observed with cells plated on tissue culture plastic. The results are reported in Table 5.

TABLE 5

Cell attachment to RAD16 and EAK16 biopolymer sheets is independent of serum and cell-secreted cell attachment factors

| Cell type-biopolymer-attachment period | medium with serum, no cyclohexamide | serum-free medium, + cyclohexamide |
|---|---|---|
| 3T3-RAD16 30 min | ++++ | ++++ |
| 3T3-RAD16 60 min | ++++ | ++++ |
| 3T3-RAD16 8 hrs | ++++ | ++ |
| 3T3-EAK16 30 min | ++++ | ++++ |
| 3T3-EAK16 60 min | ++++ | ++++ |
| 3T3-EAK16 8 hrs | ++++ | ++ |

++++ = strong attachment; +++ = moderate attachment
++ = weak attachment; +/− = little or no attachment Cells were pretreated in serum-free medium containing 30 μg/ml cyclohexamide for 2 hours before introduction to the peptide membranes. The cells used for the calcium and magnesium-free condition were pre-equilibrated in $Ca^{++}$ and $Mg^{++}$ free medium containing 5 mM EDTA for 15 minutes before introduction to the peptide membranes. Cells were allowed to attach to the peptide membranes for 30 minutes, 1 and 8 hours at 37° C. The attached cells were shaken for 10 minutes on a rotary rocker at 60 r.p.m., then scored under phase contrast microscopy. The results are reported in Table 6.

TABLE 6

Cell attachment to RAD16 and EAK16 biopolymer sheets is integrin-independent[+] occurs in $Ca^{++}$ and $Mg^{++}$ free medium

| Cell type-biopolymer attachment period | Normal $Ca^{++}$ & $Mg^{++}$ serum-free + Cyclohex | $Ca^{++}$ & $Mg^{++}$ free, EDTA serum-free + Cyclohex |
|---|---|---|
| 3T3-RAD16 30 min | ++++ | +++ |
| 3T3-RAD16 30 min | ++++ | ++++ |
| 3T3-EAK16 30 min | ++++ | ++++ |
| 3T3-EAK16 60 min | ++++ | ++++ |
| PC12-RAD16 30 min | ++++ | ++++ |
| PC12-RAD16 60 min | ++++ | ++++ |
| PC12-EAK16 30 min | ++++ | ++++ |
| PC12-EAK16 60 min | ++++ | ++++ |
| PC12$_{NGF}$RAD16 30 min | ++++ | ++++ |
| PC12$_{NGF}$RAD16 60 min | ++++ | ++++ |
| PC12$_{NGF}$EAR16 30 min | ++++ | ++++ |
| PC12$_{NGF}$EAR16 60 min | ++++ | ++++ |

++++ = strong attachment; +++ = moderate attachment
++ = weak attachment; +/− = little or no attachment The membranes were formed by addition of the oligopeptides to the cell culture media in the presence of 10 μg/ml Congo red. The cells were then applied to the culture media and allowed attachment to the peptide-membranes at 37° C.

for 2–3 hours. The visible membranes were transferred to another set of culture media. Cells on membranes were observed under a phase contrast microscope every two days for two weeks.

TABLE 7

Cells Attached on the Self-Complementary Oligopeptide-Membrane

| Cell Type | Cell Line | EAK16 | RAD16 | RADA16 | EAK16/RAD16 |
|---|---|---|---|---|---|
| Mouse Fibroblast | NIH-3T3 | +++ | ++++ | ++ | ++ |
| Chick Embryo Fibroblast | CEF | +++ | ++++ | ++++ | +++ |
| Human Foreskin Fibroblast | HFF | +++ | ++++ | ++++ | +++ |
| Chinese Hamster Ovary | CHO | +++ | ++++ | ++++ | +++ |
| Human Cervix Fibroblast | Hela (HLB6) | +++ | ++++ | ++++ | +++ |
| Human Bone | MG63 | +++ | ++++ | ++++ | +++ |
| Human Liver | HepG2 | +++ | ++++ | ++++ | +++ |
| Hamster Pancrease | HIT-T15 | ++ | +++ | N/D | ++ |
| Rat Neuron | PC12 | +++ | ++++ | ++++ | ++++ |
| Rat Neuron NGF-differentiated | PC12/NGF | +++ | ++++ | N/D | ++++ |
| Human Neuroblastoma | SH-SY5Y | +++++ | +++++ | N/D | N/D |
| Mouse Cerebellum Granule Cells | | +++++ | +++++ | N/D | N/D |
| Human Keratinocytes | | ++ | +++ | N/D | N/D |

EXAMPLE 7

In Vitro Neurite Outgrowth

The suitability of these materials for supporting in vitro neurite outgrowth was tested by treating biomaterial-attached PC12 cells with nerve growth factor (NGF). This treatment induces PC12 cells to differentiate into sympathetic neurons which can send out long processes called neurites. There was a marked difference in the neurite promoting properties of the two materials tested (EAK16 and RAD16). Nerve growth factor treated PC12 cells sent out robust neurite processes on the RAD16 membranes, while little neurite processes were seen on the EAK16 membranes.

Nerve growth factor differentiated PC12 cells have been used extensively in studies of neurite outgrowth. PC12 cells upregulate the number of calcium-dependent and -independent cell adhesion receptors in response to nerve growth factor. Cell attachment and neurite outgrowth from nerve growth factor differentiated PC12 cells was examined on membranes of RAD16 and EAK16 in order to determine whether membranes containing RGD-like sequences would preferentially support these cell activities. Neurite outgrowth on peptide membranes is of interest for potential applications of nerve repair.

Untreated PC12 cells were introduced to peptide membranes of EAK16 and RAD16 suspended in 85% RMMP1, 10% heat inactivated horse serum, 5% fetal bovine serum. Half of the cells were treated with nerve growth factor (50 ng/ml, NGF) and were supplemented with NGF every 3–4 days for 14 days. Robust neurite outgrowth was observed from NGF-treated cells on the tissue culture plastic and the NGF-treated cells on the RAD16 membrane. The neurite outgrowth reached greater than 400 $\mu$m in length, approximately 15–20 times the cell body, following the contour of the matrices in a three dimensional network. Neurite outgrowth was absent for all untreated groups and little neurite outgrowth was seen on and NGF-treated EAK16 groups.

TABLE 8

Neurite outgrowth from untreated and nerve growth factor treated PC12 cells on EAK16 and RAD16 biopolymers and tissue culture plastic

| Biopolymer | untreated, 14 days | NGF treated, 14 days |
|---|---|---|
| EAK16 | – | –1+ |
| RAD16 | – | ++++ |

++++ = robust neurite outgrowth,
– = no neurite outgrowth
–1+ = little neurite outgrowth.
The experiment was repeated with retonic acid - differentiated human neuroblastotne and mouse cerebellum granule primary cells with similar results and less robustly (e.g., 50–100 $\mu$m in length) with primary chicken dorsal root ganglion cells.

EXAMPLE 8

In order for a biomaterial to be useful for transplantation, it must be shown that the material is non-toxic in vivo. Non-antigenicity is another desirable property in order to limit host rejection. Attempts to raise polyclonal antibodies against EAK16 peptides and EAK16-conjugated proteins in rabbits have been unsuccessful to date. This indicates that this material is non-immunogenic. Experiments have begun to examine the in vivo response to tissue injections of RAK16 and RAD16 in vivo. Gliosis is a well characterized reaction which occurs in the brain in response to toxic insult. Inflammation and necrosis occur in other tissues in response to toxic insult. In vivo injections of EAK16 and RAD16 are believed to be non-toxic as shown by the absence of gliosis following injections into brain. Additionally, in vivo injections of EAK16 and RAD16 into muscle did not elicit a discernable inflammatory response.

In vivo injections of EAK16 and RAD16

Three hundred g rats were anesthesized with equithesin (0.3 ml/100 g body weight). The skull was surgically exposed and small burr holes were stereotaxically drilled at AP=+1.5, ML=+/–3.0 relative to bregma. An injection cannula was placed at a depth of –4.5 in the striatum (a brain structure). Experimental rats received 1 $\mu$l of EAK16 or RAD16 injected into the striatum. Control rats received similar injections of ibotenic acid, a well characterized toxin, as a positive control for gliosis. The experimental rats also received 35 $\mu$l injection of EAK16 or RAD16 into the thigh muscle (n=2 for each group). The rats were allowed to recover, then sacrificed for tissue harvest. Brain sections were prepared used a freezing microtome and processed for nissl stain which reveals normal cell bodies and gliotic scarring. Control rats which received brain ibotenic acid injections showed robust gliotic scarring around the injection site. No such reaction was observed in the rats which received injections of EAK16 or RAD16. The muscle tissue of rats which received muscle injections of EAK16 or RAD16 did not exhibit discernable inflammation or necrosis. These preliminary results indicate that EAK16 and RAD16 elicit little or no toxicity in vivo.

In summary, these novel peptide membranes can support cell attachment and growth, as well as specialized functions such as neurite outgrowth. The combination of unique physical and cell growth promoting properties of these biomaterials hold significant promise for their utility for industrial cell culture and biomedical technologies.

REFERENCES

Azorin et al., *Proc. Nat. Acad. Sci. USA* 81:5714–5718 (1984)
Bairoch, *Nucleic Acids Res.* 19 supp.:2241–2245 (1991)
Barrow and Zagorski, *Science* 253:179–182 (1991)
Behe and Felsenfeld, *Proc. Natl. Acad. Sci. USA* 78:1619–1623 (1981)
Bianchi et al., *EMBO J.* 11:1055–1063 (1992)
Blaho and Wells, *J. Biol. Chem.* 262:6082–6088 (1987)
Blumberg and Silver, *Nature* 349:627–629 (1991)
Brack and Orgel, *Nature* 256:383–387 (1975)
Bullock et al., *Mol. Cell. Biol.*, 6:3948–3953 (1986)
Caplan and Douglas, *J. Cell Biol.* 114:609–621 (1991)
Celenza and Carlson, *Science* 233:1175–1180 (1986)
Chou and Fasman, *Annu. Rev. Biochem.* 47:251–276 (1978)
Churchill and Travers, *Trends Biochem. Sci.* 183:92–97 (1991)
Erickson, *Scientific American*, September 1992, pp. 163–164
Fishel et al., *Proc. Natl. Acad. Sci. USA* 85:36–40 (1988)
Gay et al., *FEBS Letters* 291:87–91 (1991)
Halverson et al., *Biochemistry* 29:2639–2644 (1990)
Hamada et al., *Proc. Natl. Acad. Sci. USA* 79:6465–6469 (1982)
Hilbich et al., *J. Mol. Biol.* 50:149–165 (1991)
Iqbal and Wisniewski, in: *Alzheimer's Disease: The Standard Reference*, Reisberg (ed.), Free Press, Collier Macmillan Publishers, London, 1983, pp. 48–56
Jaworski et al., *Science* 238:773–777 (1987)
Jones, *Genetics* 85:23–33 (1977)
Kirschner et al., *Proc. Natl. Acad. Sci. USA* 84:6953–6957 (1987)
Laemmli, *Nature* 227:680–682 (1970)
Lafer et al., *EMBO J.* 4:3655–3660 (1985)
Lechner and Carbon, *Cell* 64:717–725 (1991)
Liberek et al., *Proc. Natl. Acad. Sci. USA* 85:6632–6636 (1988)
Lilley, *Nature* 357:282–283 (1991)
Liu and Wang, *Proc. Natl. Acad. Sci. USA* 84:7024–7028 (1987)
Lizardi, *Cell* 18:581–589 (1979)
Luke et al., *J. Cell Biol.* 114:623–638 (1991)
Maniatis et al., *Molecular Cloning: A Laboratory Manual*, Cold Spring Harbor Laboratory Press, Cold Spring Harbor, New York, 1982
Marqusee and Baldwin, *Proc. Natl. Acad. Sci. USA* 84:8898–8902 (1987)
Marqusee et al., *Proc. Natl. Acad. Sci USA* 86:5286–5290 (1989)
McCarthy and Heywood, *Nucleic Acids Res.* 15:8069–8085 (1987)
Moller et al., *J. Biol. Chem.* 257:12081–12085 (1982)
Moreno and Nurse, *Cell* 61:5 49–551 (1990)
Mura and Stollar, *Biochemistry* 23:6147–6152 (1984)
Naylor and Clark, *Nucleic Acids Res.* 18:1595–1601 (1990)
Nordheim and Rich, *Nature* 303:674–679 (1983)
Osterman and Kaiser, *J. Cell. Biochem.* 29:57–72 (1985)
Pabo and Sauer, *Annu. Rev. Biochem.* 53:293–322 (1984)
Padmanabhan et al., *Nature* 344:268–270 (1991)
Pauling, *Nature of the Chemical Bond and the Structure of Molecules and Crystals: An Introduction to Model Structural Chemistry*, 3rd ed., Cornell University Press, Ithaca, New York, 1960
Pears, *Histochemistry, Theoretical and Applied*, 2nd Ed., Little, Brown and Company, Boston, 1960
Peck et al., *Proc. Natl. Acad. Sci. USA* 79:4560–4564 (1982)
Piggion et al., *Biopolymers* 11:633–643 (1972)
Raabe and Manley, *Nucleic Acids Res.* 19:6645 (1991)
Rahmouni and Wells, *Science* 246:358–363 (1989)
Rich et al., *Annu. Rev. Biochem.* 53:791–864 (1984)
Rippon et al., *J. Mol. Biol.* 75:369–375 (1973)
Robbins et al., *Cell* 64:615–623 (1991)
Rothstein, *Methods Enzymol.* 101:202–211 (1983)
Rott et al., *Virology* 165:74–86 (1988)
Russell et al., *EMBO J.* 2:1647–1653 (1983)
Sadler et al., *J. Cell Biol.* 109:2665–2675 (1989)
Sambrook et al., *Molecular Cloning: A Laboratory Manual* 2nd Ed., Cold Spring Harbor Laboratory press, Cold Spring Harbor, N.Y., 1989
Sanger et al., *Proc. Natl. Acad. Sci. USA* 74:5463–5467 (1977)
Seeman et al., *Proc. Natl. Acad. Sci. USA* 73:804–808 (1976)
Seipke et al., *Biopolymers* 13:1621–1633 (1974)
Sharp et al., *Nucleic Acids Res.* 14:5125–5143 (1986)
Sherman et al., *Methods in Yeast Genetics*, Cold Spring Harbor Laboratory Press, Cold Spring Harbor, N.Y., 1986
St. Pierre et al., *Biopolymers* 17:1837–1847 (1978)
Studier et al., *Methods Enzymol.* 185:60–89 (1990)
Takeuchi et al., *FEBS Letters* 279:253–255 (1991)
Treco and Arnheim, *Mol. Cell Biol.* 6:3943–3947 (1986)
Trudelle, *Polymer* 16:9–15 (1975)
Tsao et al., *Cell* 56:111–118 (1989)
Vardimon and Rich, *Proc. Natl. Acad. Sci. USA* 81:3268–3272 (1983)
Wahls et al., *Mol. Cell Biol.* 10:785–793 (1990)
Winter and Varshavsky, *EMBO J.* 8:1867–1877 (1989)
Wittig et al., *J. Cell Biol.* 108:755–761 (1989)
Wood et al., *Proc. Natl. Acad. Sci. USA* 82:1585–1588 (1985)
Zinsmaier et al., *J. Neurogenet.* 7:15–29 (1990)
Zylicz et al., *EMBO J.* 8:1601–1608

Equivalents

Those skilled in the art will know, or be able to ascertain using no more than routine experimentation, many equivalents to the specific embodiments of the invention described herein. These and all other equivalents are intended to be encompassed by the following claims.

SEQUENCE LISTING (1) GENERAL INFORMATION:

(iii) NUMBER OF SEQUENCES: 64

(2) INFORMATION FOR SEQ ID NO:1:

(i) SEQUENCE CHARACTERISTICS:

(A) LENGTH: 3083 base pairs
(B) TYPE: nucleic acid
(C) STRANDEDNESS: double
(D) TOPOLOGY: linear (ii) MOLECULE TYPE: DNA (genomic)

(ix) FEATURE:
(A) NAME/KEY: CDS
(B) LOCATION: 1292..2590
(D) OTHER INFORMATION: /product= "zuotin"

(xi) SEQUENCE DESCRIPTION: SEQ ID NO:1:

```
CCAAAGTGAA TGATATGGGG CTAGAAACGT GTGTTACTTT AGGTATGGTT GATCAAGATC      60

AAGCAAAGCA ATTGAAAGAT GCAGGTTTGA CTGCATACAA CCATAACATC GACACTTCCA     120

GAGAACACTA TAGTAAGGTC ATCACCACGA GAACCTACGA CGACAGGTTA CAGACCATCA     180

AGAATGTCCA AGAATCTGGA ATAAAAGCCT GTACCGGTGG TATTTTGGGT CTCGGTGAAA     240

GCGAAGACGA CCATATAGGA TTCATCTACA CATTATCCAA TATGTCTCCT CATCCTGAGT     300

CCCTACCAAT TAATAGACTA GTTGCTATCA AAGGGACTCC AATGGCTGAG GAACTTGCCG     360

ATCCAAAGAG TAAAAAGTTG CAATTCGACG AAATTTTGAG AACCATTGCC ACAGCGAGAA     420

TAGTTATGCC AAAGGCCATT ATAAGACTTG CCGCTGGTCG TTATACAATG AAAGAAACAG     480

AGCAATTTGT CTGTTTCATG GCAGGTTGTA ACAGTATCTT CACCGGTAAG AAAATGCTGA     540

CGACAATATA TAACGGTTGG GACGAAGACA AGGCAATGTT GGCTAAATGG GGATTGCAAC     600

CTATGGAGGC ATTTAAGTAC GACAGATCTT GAAGATAGGG ATATGTGGAT AATTCTACGA     660

TTCTAACTGT ACATTTCTCC CTTATTTATT AAGAAAACCT ATATATATAT ATATTTACCT     720

ATTTATTCTG CCATCGTTAG CTGGCGTTTT ATCTTTTATG CATCCAATAT CTAATATTAC     780

TTCCGATCAC GCATTTAGTT CTGATTACAG CAGAAATCGT AGCGCGATGA GACATTTCAT     840

CAAATGGCCT TTTTTTTTTG GGCAATTTTT TTATATCTTG AAATGATAGT TGCCTTGTAC     900

TTTCAACCGT TCATTTCATT AAGAACTTGA CTAAATATGA ACATTTCTTA AAAAAAAAGG     960

TTGACATATA AAAATAATCG AATATAAACG ATGGAATTTT TATAAAATTA AACACATATA    1020

TATATATATA TTAACTATAA ATATGTCAAA GAAACCATAC AATCATAGAT TTATAACTAT    1080

CTTTTGGATG ACATTAATGA ACATAACGCT CCTAATACAA ATGTCAAAAA ATATTACCCG    1140

CAAATACGAA TCTTTTTTTT TTCTCGATGA AATTTTGCAA AGAGTTCGAA ATTTTTATTT    1200

CAAGAGCTGG TAGAGAAAAT TTCATAAGGT TTTCCTACCG ATGCTTTTAT AAAATCTTCG    1260

TTTTGTCTCA CATATACCAA CAAGAGTAAC G ATG TTT TCT TTA CCT ACC CTA       1312
                                  Met Phe Ser Leu Pro Thr Leu
                                   1               5

ACC TCA GAC ATC ACT GTT GAA GTC AAC AGT TCC GCT ACC AAA ACC CCA      1360
Thr Ser Asp Ile Thr Val Glu Val Asn Ser Ser Ala Thr Lys Thr Pro
            10                  15                  20

TTC GTC CGT CGT CCG GTC GAA CCG GTT GGT AAG TTC TTT TTG CAA CAT      1408
Phe Val Arg Arg Pro Val Glu Pro Val Gly Lys Phe Phe Leu Gln His
    25                  30                  35

GCT CAA AGA ACT TTG AGA AAC CAC ACC TGG TCT GAA TTT GAA AGA ATT      1456
Ala Gln Arg Thr Leu Arg Asn His Thr Trp Ser Glu Phe Glu Arg Ile
40                  45                  50                  55

GAA GCT GAA AAG AAC GTC AAA ACC GTT GAT GAA TCC AAT GTC GAC CCA      1504
Glu Ala Glu Lys Asn Val Lys Thr Val Asp Glu Ser Asn Val Asp Pro
                60                  65                  70

GAT GAG TTG TTA TTC GAC ACT GAA TTG GCC GAT GAA GAT TTA CTG ACT      1552
Asp Glu Leu Leu Phe Asp Thr Glu Leu Ala Asp Glu Asp Leu Leu Thr
        75                  80                  85
```

```
CAT GAT GCT AGA GAC TGG AAA ACT GCC GAT TTG TAT GCT GCT ATG GGT         1600
His Asp Ala Arg Asp Trp Lys Thr Ala Asp Leu Tyr Ala Ala Met Gly
             90                  95                 100

TTG TCT AAG TTG CGT TTC AGA GCT ACT GAA AGT CAA ATC ATC AAG GCT         1648
Leu Ser Lys Leu Arg Phe Arg Ala Thr Glu Ser Gln Ile Ile Lys Ala
        105                 110                 115

CAC AGA AAA CAA GTT GTC AAG TAC CAT CCA GAC AAG CAA TCT GCT GCT         1696
His Arg Lys Gln Val Val Lys Tyr His Pro Asp Lys Gln Ser Ala Ala
120                 125                 130                 135

GGT GGT AGT TTG GAC CAA GAT GGC TTT TTC AAG ATT ATT CAA AAG GCC         1744
Gly Gly Ser Leu Asp Gln Asp Gly Phe Phe Lys Ile Ile Gln Lys Ala
                140                 145                 150

TTT GAA ACT TTG ACT GAT TCC AAC AAG AGA GCT CAG TAC GAC TCA TGT         1792
Phe Glu Thr Leu Thr Asp Ser Asn Lys Arg Ala Gln Tyr Asp Ser Cys
            155                 160                 165

GAT TTT GTT GCC GAT GTT CCT CCT CCA AAG AAG GGT ACC GAT TAT GAC         1840
Asp Phe Val Ala Asp Val Pro Pro Pro Lys Lys Gly Thr Asp Tyr Asp
        170                 175                 180

TTT TAT GAA GCT TGG GGC CCC GTT TTC GAA GCT GAA GCT CGT TTT TCT         1888
Phe Tyr Glu Ala Trp Gly Pro Val Phe Glu Ala Glu Ala Arg Phe Ser
185                 190                 195

AAG AAG ACT CCT ATT CCT TCT CTA GGT AAC AAA GAT TCT TCC AAG AAG         1936
Lys Lys Thr Pro Ile Pro Ser Leu Gly Asn Lys Asp Ser Ser Lys Lys
200                 205                 210                 215

GAA GTT GAA CAA TTC TAT GCT TTC TGG CAC AGA TTT GAC TCC TGG AGA         1984
Glu Val Glu Gln Phe Tyr Ala Phe Trp His Arg Phe Asp Ser Trp Arg
                220                 225                 230

ACC TTT GAG TTC TTG GAC GAA GAT GTC CCA GAT GAC TCT TCT AAC AGA         2032
Thr Phe Glu Phe Leu Asp Glu Asp Val Pro Asp Asp Ser Ser Asn Arg
            235                 240                 245

GAC CAC AAG CGT TAC ATT GAA AGA AAG AAC AAG GCC GCA AGA GAC AAG         2080
Asp His Lys Arg Tyr Ile Glu Arg Lys Asn Lys Ala Ala Arg Asp Lys
        250                 255                 260

AAG AAG ACT GCT GAT AAC GCT AGA TTG GTC AAA CTT GTT GAA AGA GCT         2128
Lys Lys Thr Ala Asp Asn Ala Arg Leu Val Lys Leu Val Glu Arg Ala
265                 270                 275

GTC AGT GAA GAT CCC CGT ATC AAA ATG TTC AAA GAA GAA GAG AAG AAG         2176
Val Ser Glu Asp Pro Arg Ile Lys Met Phe Lys Glu Glu Glu Lys Lys
280                 285                 290                 295

GAA AAG GAA AGA AGA AAA TGG GAA AGA GAA GCC GGT GCC AGA GCT GAA         2224
Glu Lys Glu Arg Arg Lys Trp Glu Arg Glu Ala Gly Ala Arg Ala Glu
                300                 305                 310

GCT GAA GCT AAG GCC AAG GCC GAA GCT GAA GCG AAG GCT AAA GCT GAA         2272
Ala Glu Ala Lys Ala Lys Ala Glu Ala Glu Ala Lys Ala Lys Ala Glu
            315                 320                 325

TCT GAA GCC AAG GCT AAC GCC TCC GCA AAA GCT GAC AAA AAG AAG GCT         2320
Ser Glu Ala Lys Ala Asn Ala Ser Ala Lys Ala Asp Lys Lys Lys Ala
        330                 335                 340

AAG GAA GCT GCT AAG GCC GCC AAG AAA AAG AAC AAG AGA GCC ATC CGT         2368
Lys Glu Ala Ala Lys Ala Ala Lys Lys Lys Asn Lys Arg Ala Ile Arg
345                 350                 355

AAC TCT GCT AAG GAA GCT GAC TAC TTT GGT GAT GCT GAC AAG GCC ACC         2416
Asn Ser Ala Lys Glu Ala Asp Tyr Phe Gly Asp Ala Asp Lys Ala Thr
360                 365                 370                 375

ACG ATT GAC GAA CAA GTT GGT TTG ATC GTT GAC AGT TTG AAT GAC GAA         2464
Thr Ile Asp Glu Gln Val Gly Leu Ile Val Asp Ser Leu Asn Asp Glu
                380                 385                 390

GAG TTA GTG TCC ACC GCC GAT AAG ATC AAG GCC AAT GCT GCT GGT GCC         2512
Glu Leu Val Ser Thr Ala Asp Lys Ile Lys Ala Asn Ala Ala Gly Ala
            395                 400                 405
```

```
AAG GAA GTT TTG AAG GAA TCT GCA AAG ACT ATT GTC GAT TCT GGC AAA          2560
Lys Glu Val Leu Lys Glu Ser Ala Lys Thr Ile Val Asp Ser Gly Lys
         410                 415                 420

CTA CCA TCC AGC TTG TTG TCC TAC TTC GTG TGAATACCGT AAGAAATGGA            2610
Leu Pro Ser Ser Leu Leu Ser Tyr Phe Val
425                 430

ATAGAATATA TACGAATGTA TACGAATATT ATAGAGAACG TTCTCTTTTA TTTCTATAAT        2670

GAATAGGTTC GGGTAACGGT TCCCTTTTTA GGTATTTCTA GAAGATGAGA GAAGAGGGAA        2730

TAATGAGAAA GGCGAAAAAT AAAGACACCT TTAACGAAAG ATCAAGGTG TCCTTATTTA         2790

CTTACAATAG CTGCAATTAG TACGACTCAA AAAAAGTGAA AACAAAACTG AAAGGATAGA       2850

TCAATGTCTT ACAGAGGACC TATTGGAAAT TTTGGCGGAT AGCCAATGTC ATCATCGCTT        2910

GGACCATACT CTGGCGGTGC ACAATTCCGA TCAAACCAGA ACCAATCCAC TTCTGGCATC        2970

TTAAAGCAAT GGAAGCATTC TTTTGAAAAG TTTGCCTCCA GAATTGAGGG GCTCACTGAC        3030

AATGCAGTTG TTTATAAATT GAAGCCTTAC ATTCCAAGTT TGTCAAGATT TTT              3083
```

(2) INFORMATION FOR SEQ ID NO:2:

(i) SEQUENCE CHARACTERISTICS:
       (A) LENGTH: 433 amino acids
       (B) TYPE: amino acid
       (D) TOPOLOGY: linear (ii) MOLECULE TYPE: protein (xi) SEQUENCE DESCRIPTION: SEQ ID NO:2:

```
Met Phe Ser Leu Pro Thr Leu Thr Ser Asp Ile Thr Val Glu Val Asn
1               5                   10                  15

Ser Ser Ala Thr Lys Thr Pro Phe Val Arg Arg Pro Val Glu Pro Val
            20                  25                  30

Gly Lys Phe Phe Leu Gln His Ala Gln Arg Thr Leu Arg Asn His Thr
        35                  40                  45

Trp Ser Glu Phe Glu Arg Ile Glu Ala Glu Lys Asn Val Lys Thr Val
    50                  55                  60

Asp Glu Ser Asn Val Asp Pro Asp Glu Leu Leu Phe Asp Thr Glu Leu
65                  70                  75                  80

Ala Asp Glu Asp Leu Leu Thr His Asp Ala Arg Asp Trp Lys Thr Ala
                85                  90                  95

Asp Leu Tyr Ala Ala Met Gly Leu Ser Lys Leu Arg Phe Arg Ala Thr
            100                 105                 110

Glu Ser Gln Ile Ile Lys Ala His Arg Lys Gln Val Val Lys Tyr His
        115                 120                 125

Pro Asp Lys Gln Ser Ala Ala Gly Gly Ser Leu Asp Gln Asp Gly Phe
    130                 135                 140

Phe Lys Ile Ile Gln Lys Ala Phe Glu Thr Leu Thr Asp Ser Asn Lys
145                 150                 155                 160

Arg Ala Gln Tyr Asp Ser Cys Asp Phe Val Ala Asp Val Pro Pro Pro
                165                 170                 175

Lys Lys Gly Thr Asp Tyr Asp Phe Tyr Glu Ala Trp Gly Pro Val Phe
            180                 185                 190

Glu Ala Glu Ala Arg Phe Ser Lys Lys Thr Pro Ile Pro Ser Leu Gly
        195                 200                 205

Asn Lys Asp Ser Ser Lys Lys Glu Val Glu Gln Phe Tyr Ala Phe Trp
    210                 215                 220

His Arg Phe Asp Ser Trp Arg Thr Phe Glu Phe Leu Asp Glu Asp Val
225                 230                 235                 240
```

```
Pro Asp Asp Ser Ser Asn Arg Asp His Lys Arg Tyr Ile Glu Arg Lys
            245                 250                 255
Asn Lys Ala Ala Arg Asp Lys Lys Thr Ala Asp Asn Ala Arg Leu
            260                 265                 270
Val Lys Leu Val Glu Arg Ala Val Ser Glu Asp Pro Arg Ile Lys Met
            275                 280                 285
Phe Lys Glu Glu Glu Lys Lys Glu Lys Glu Arg Arg Lys Trp Glu Arg
            290                 295                 300
Glu Ala Gly Ala Arg Ala Glu Ala Glu Ala Lys Ala Lys Ala Glu Ala
305                 310                 315                 320
Glu Ala Lys Ala Lys Ala Glu Ser Glu Ala Lys Ala Asn Ala Ser Ala
                325                 330                 335
Lys Ala Asp Lys Lys Ala Lys Glu Ala Lys Ala Ala Lys Lys
                340                 345                 350
Lys Asn Lys Arg Ala Ile Arg Asn Ser Ala Lys Glu Ala Asp Tyr Phe
                355                 360                 365
Gly Asp Ala Asp Lys Ala Thr Thr Ile Asp Glu Gln Val Gly Leu Ile
    370                 375                 380
Val Asp Ser Leu Asn Asp Glu Glu Leu Val Ser Thr Ala Asp Lys Ile
385                 390                 395                 400
Lys Ala Asn Ala Ala Gly Ala Lys Glu Val Leu Lys Glu Ser Ala Lys
                405                 410                 415
Thr Ile Val Asp Ser Gly Lys Leu Pro Ser Ser Leu Leu Ser Tyr Phe
                420                 425                 430
Val (2) INFORMATION FOR SEQ ID NO:3:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:3:

Ala Arg Ala Arg Ala Asp Ala Asp Ala Arg Ala Arg Ala Asp Ala Asp
1               5                   10                  15

(2) INFORMATION FOR SEQ ID NO:4:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:4:

Asp Ala Glu Phe Arg His Asp Ser Gly Tyr Glu Val His His Gln Lys
1               5                   10                  15
Leu Val Phe Phe Ala Glu Asp Val Gly Ser Asn Lys
                20                  25

(2) INFORMATION FOR SEQ ID NO:5:

(i) SEQUENCE CHARACTERISTICS:
        (A) LENGTH: 11 amino acids
        (B) TYPE: amino acid
        (D) TOPOLOGY: linear
```

(ii) MOLECULE TYPE: peptide (xi) SEQUENCE DESCRIPTION: SEQ ID NO:5:

Gly Ser Asn Lys Gly Ala Ile Ile Gly Leu Met
1               5                   10

(2) INFORMATION FOR SEQ ID NO:6:

(i) SEQUENCE CHARACTERISTICS:
                 (A) LENGTH: 9 amino acids
                 (B) TYPE: amino acid
                 (D) TOPOLOGY: linear (ii) MOLECULE TYPE: peptide (xi) SEQUENCE DESCRIPTION: SEQ ID NO:6:

Arg Pro Lys Gln Gln Phe Gly Leu Met
1               5

(2) INFORMATION FOR SEQ ID NO:7:

(i) SEQUENCE CHARACTERISTICS:
                 (A) LENGTH: 9 amino acids
                 (B) TYPE: amino acid
                 (D) TOPOLOGY: linear (ii) MOLECULE TYPE: peptide (xi) SEQUENCE DESCRIPTION: SEQ ID NO:7:

Arg Pro Lys Pro Gln Gln Trp Leu Leu
1               5

(2) INFORMATION FOR SEQ ID NO:8:

(i) SEQUENCE CHARACTERISTICS:
                 (A) LENGTH: 52 amino acids
                 (B) TYPE: amino acid
                 (D) TOPOLOGY: linear (ii) MOLECULE TYPE: protein (xi) SEQUENCE DESCRIPTION: SEQ ID NO:8:

Ala Glu Glu Arg Glu Ile Arg Lys Ala Tyr Lys Arg Leu Ala Met Lys
1               5                   10                  15

Tyr His Pro Asp Arg Asn Gln Gly Asp Lys Glu Ala Glu Ala Lys Phe
                20                  25                  30

Lys Glu Ile Lys Glu Ala Tyr Glu Val Leu Thr Asp Ser Gln Lys Arg
            35                  40                  45

Ala Ala Tyr Asp
        50

(2) INFORMATION FOR SEQ ID NO:9:

(i) SEQUENCE CHARACTERISTICS:
                 (A) LENGTH: 52 amino acids
                 (B) TYPE: amino acid
                 (D) TOPOLOGY: linear (ii) MOLECULE TYPE: protein (xi) SEQUENCE DESCRIPTION: SEQ ID NO:9:

Ala Thr Glu Lys Glu Ile Lys Ser Ala Tyr Arg Gln Leu Ser Lys Lys
1               5                   10                  15

Tyr His Pro Asp Lys Asn Ala Gly Ser Glu Glu Ala His Gln Lys Phe
                20                  25                  30

Ile Glu Val Gly Glu Ala Tyr Asp Val Leu Ser Asp Pro Glu Lys Lys

```
                35                  40                  45
Lys Ile Tyr Asp
 50
```

(2) INFORMATION FOR SEQ ID NO:10:

(i) SEQUENCE CHARACTERISTICS:
        (A) LENGTH: 52 amino acids
        (B) TYPE: amino acid
        (D) TOPOLOGY: linear (ii) MOLECULE TYPE: protein (xi) SEQUENCE DESCRIPTION: SEQ ID NO:10:

```
Ala Thr Gly Asp Asp Ile Lys Lys Thr Tyr Arg Lys Leu Ala Leu Lys
 1               5                  10                  15

Tyr His Pro Asp Lys Asn Pro Asp Asn Val Asp Ala Ala Asp Lys Phe
                20                  25                  30

Lys Glu Val Asn Arg Ala His Ser Ile Leu Ser Asp Gln Thr Lys Arg
                35                  40                  45

Asn Ile Tyr Asp
 50
```

(2) INFORMATION FOR SEQ ID NO:11:

(i) SEQUENCE CHARACTERISTICS:
        (A) LENGTH: 49 amino acids
        (B) TYPE: amino acid
        (D) TOPOLOGY: linear (ii) MOLECULE TYPE: protein (xi) SEQUENCE DESCRIPTION: SEQ ID NO:11:

```
Ala Asn Glu Gln Glu Leu Lys Lys Gly Tyr Arg Lys Ala Ala Leu Lys
 1               5                  10                  15

Tyr His Pro Asp Lys Pro Thr Gly Asp Thr Glu Lys Phe Lys Glu Ile
                20                  25                  30

Ser Glu Ala Phe Glu Ile Leu Asn Asp Pro Gln Lys Arg Glu Ile Tyr
                35                  40                  45

Asp
```

(2) INFORMATION FOR SEQ ID NO:12:

(i) SEQUENCE CHARACTERISTICS:
        (A) LENGTH: 51 amino acids
        (B) TYPE: amino acid
        (D) TOPOLOGY: linear (ii) MOLECULE TYPE: protein (xi) SEQUENCE DESCRIPTION: SEQ ID NO:12:

```
Ala Thr Asp Val Glu Ile Lys Lys Ala Tyr Arg Lys Cys Ala Leu Lys
 1               5                  10                  15

Tyr His Pro Asp Lys Asn Pro Ser Glu Glu Ala Ala Glu Lys Phe Lys
                20                  25                  30

Glu Ala Ser Ala Ala Tyr Glu Ile Leu Ser Asp Pro Glu Lys Arg Asp
                35                  40                  45

Ile Tyr Asp
 50
```

(2) INFORMATION FOR SEQ ID NO:13:

(i) SEQUENCE CHARACTERISTICS:

(A) LENGTH: 54 amino acids
(B) TYPE: amino acid
(D) TOPOLOGY: linear (ii) MOLECULE TYPE: protein (xi) SEQUENCE DESCRIPTION: SEQ ID NO:13:

Ala Thr Ala Ala Asp Ile Lys Thr Ala Tyr Arg Arg Thr Ala Leu Lys
1               5                  10                  15

Tyr His Pro Asp Lys Gly Gly Asp Glu Glu Lys Met Lys Glu Leu Asn
                20                  25                  30

Thr Leu Met Glu Glu Phe Arg Glu Thr Glu Gly Leu Arg Ala Asp Glu
            35                  40                  45

Thr Leu Glu Asp Ser Asp
    50

(2) INFORMATION FOR SEQ ID NO:14:

(i) SEQUENCE CHARACTERISTICS:
        (A) LENGTH: 51 amino acids
        (B) TYPE: amino acid
        (D) TOPOLOGY: linear (ii) MOLECULE TYPE: protein (xi) SEQUENCE DESCRIPTION: SEQ ID NO:14:

Ala Ser Asp Arg Asp Ile Lys Ser Ala Tyr Arg Lys Leu Ser Val Lys
1               5                  10                  15

Phe His Pro Asp Lys Leu Ala Lys Gly Leu Thr Pro Asp Glu Lys Val
                20                  25                  30

Gln Ile Thr Lys Ala Tyr Glu Ser Leu Thr Asp Glu Leu Val Arg Gln
            35                  40                  45

Asn Tyr Leu
    50

(2) INFORMATION FOR SEQ ID NO:15:

(i) SEQUENCE CHARACTERISTICS:
        (A) LENGTH: 51 amino acids
        (B) TYPE: amino acid
        (D) TOPOLOGY: linear (ii) MOLECULE TYPE: protein (xi) SEQUENCE DESCRIPTION: SEQ ID NO:15:

Ala Leu Gly Arg Gly Asp Gln Ala Gly Leu Pro Pro Gly Leu Arg
1               5                  10                  15

Tyr His Pro Asp Leu Asn Leu Glu Pro Gly Ala Glu Glu Leu Phe Leu
                20                  25                  30

Glu Ile Ala Glu Ala Tyr Asp Val Leu Ser Asp Pro Arg Leu Arg Glu
            35                  40                  45

Ile Phe Asp
    50

(2) INFORMATION FOR SEQ ID NO:16:

(i) SEQUENCE CHARACTERISTICS:
        (A) LENGTH: 60 amino acids
        (B) TYPE: amino acid
        (D) TOPOLOGY: linear (ii) MOLECULE TYPE: protein (xi) SEQUENCE DESCRIPTION: SEQ ID NO:16:

```
Lys Ala Ala Ala Lys Arg Lys Ala Ala Leu Ala Lys Lys Lys Ala Ala
1               5                   10                  15

Ala Ala Lys Arg Lys Ala Ala Ala Lys Ala Lys Ala Lys Lys Ala Lys Pro
            20                  25                  30

Lys Lys Lys Ala Ala Lys Ala Lys Lys Pro Ala Lys Lys Ser Pro
        35                  40                  45

Lys Lys Ala Lys Lys Pro Ala Lys Lys Ser Pro Lys
    50                  55                  60
```

(2) INFORMATION FOR SEQ ID NO:17:

(i) SEQUENCE CHARACTERISTICS:
        (A) LENGTH: 61 amino acids
        (B) TYPE: amino acid
        (D) TOPOLOGY: linear (ii) MOLECULE TYPE: protein (xi) SEQUENCE DESCRIPTION: SEQ ID NO:17:

```
Lys Glu Lys Ala Pro Arg Lys Arg Ala Thr Ala Ala Lys Pro Lys Lys
1               5                   10                  15

Pro Ala Ala Lys Lys Pro Ala Ala Ala Lys Lys Pro Lys Lys Ala
            20                  25                  30

Ala Ala Val Lys Lys Ser Pro Lys Lys Ala Lys Lys Pro Ala Ala Ala
        35                  40                  45

Ala Thr Lys Lys Ala Ala Lys Ser Pro Lys Lys Ala Ala
    50                  55                  60
```

(2) INFORMATION FOR SEQ ID NO:18:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:18:

CAAGAGTAAC CATGGTTTCT TTACC                         25

(2) INFORMATION FOR SEQ ID NO:19:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:19:

```
Ala Lys Ala Gln Ala Asp Ala Lys Ala Gln Ala Asp Ala Lys Ala Gln
1               5                   10                  15

Ala Asp
```

(2) INFORMATION FOR SEQ ID NO:20:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:20:

```
Val Arg Val Arg Val Asp Val Asp Val Arg Val Arg Val Asp Val Asp
1               5                   10                  15
```

(2) INFORMATION FOR SEQ ID NO:21:

(i) SEQUENCE CHARACTERISTICS:
　　　　(A) LENGTH: 16 amino acids
　　　　(B) TYPE: amino acid
　　　　(D) TOPOLOGY: linear (ii) MOLECULE TYPE: peptide (xi) SEQUENCE DESCRIPTION: SEQ ID NO:21:

```
Ala Asp Ala Asp Ala Lys Ala Lys Ala Asp Ala Asp Ala Lys Ala Lys
1               5                   10                  15
```

(2) INFORMATION FOR SEQ ID NO:22:

(i) SEQUENCE CHARACTERISTICS:
　　　　(A) LENGTH: 32 base pairs
　　　　(B) TYPE: nucleic acid
　　　　(C) STRANDEDNESS: single
　　　　(D) TOPOLOGY: linear (xi) SEQUENCE DESCRIPTION: SEQ ID NO:22:

ATGTTTTCTT TGCCAACTTT GACTTCTGAT AT                                32

(2) INFORMATION FOR SEQ ID NO:23:

(i) SEQUENCE CHARACTERISTICS:
　　　　(A) LENGTH: 11 amino acids
　　　　(B) TYPE: amino acid
　　　　(D) TOPOLOGY: linear (ii) MOLECULE TYPE: peptide (xi) SEQUENCE DESCRIPTION: SEQ ID NO:23:

```
Met Val Ser Leu Pro Thr Leu Thr Ser Asp Ile
1               5                   10
```

(2) INFORMATION FOR SEQ ID NO:24:

(i) SEQUENCE CHARACTERISTICS:
　　　　(A) LENGTH: 12 amino acids
　　　　(B) TYPE: amino acid
　　　　(D) TOPOLOGY: linear (ii) MOLECULE TYPE: peptide (xi) SEQUENCE DESCRIPTION: SEQ ID NO:24:

```
Ala Glu Ala Lys Ala Glu Ala Glu Ala Lys Ala Lys
1               5                   10
```

(2) INFORMATION FOR SEQ ID NO:25:

(i) SEQUENCE CHARACTERISTICS:
　　　　(A) LENGTH: 16 amino acids
　　　　(B) TYPE: amino acid
　　　　(D) TOPOLOGY: linear (ii) MOLECULE TYPE: peptide (xi) SEQUENCE DESCRIPTION: SEQ ID NO:25:

```
Lys Ala Lys Ala Lys Ala Lys Ala Lys Ala Lys Ala Lys Ala Lys Ala
1               5                   10                  15
```

(2) INFORMATION FOR SEQ ID NO:26:

(i) SEQUENCE CHARACTERISTICS:
　　　　(A) LENGTH: 16 amino acids
　　　　(B) TYPE: amino acid (D) TOPOLOGY: linear (ii) MOLECULE TYPE: peptide (xi) SEQUENCE DESCRIPTION: SEQ ID NO:26:

Glu Ala Glu Ala Glu Ala Glu Ala Glu Ala Glu Ala Glu Ala Glu Ala
1               5                  10                  15

(2) INFORMATION FOR SEQ ID NO:27:

(i) SEQUENCE CHARACTERISTICS:
           (A) LENGTH: 16 amino acids
           (B) TYPE: amino acid
           (D) TOPOLOGY: linear (ii) MOLECULE TYPE: peptide (xi) SEQUENCE DESCRIPTION: SEQ ID NO:27:

Ala Asp Ala Asp Ala Asp Ala Asp Ala Asp Ala Asp Ala Asp Ala Asp
1               5                  10                  15

(2) INFORMATION FOR SEQ ID NO:28:

(i) SEQUENCE CHARACTERISTICS:
           (A) LENGTH: 56 amino acids
           (B) TYPE: amino acid
           (D) TOPOLOGY: linear (ii) MOLECULE TYPE: protein (ix) FEATURE:
           (A) NAME/KEY: negatively charged amino acid
           (B) LOCATION: 3, 5, 28, 42, 48

(ix) FEATURE:
           (A) NAME/KEY: non-conserved amino acid
           (B) LOCATION: 4, 11, 24, 25, 26, 27, 30, 32, 35, 38, 39, 49,
               50, 53

(ix) FEATURE:
           (A) NAME/KEY: non-polar amino acid
           (B) LOCATION: 14, 37, 43, 54

(xi) SEQUENCE DESCRIPTION: SEQ ID NO:28:

Ala Thr Xaa Xaa Xaa Ile Lys Lys Ala Tyr Xaa Arg Lys Xaa Ala Leu
1               5                  10                  15

Lys Tyr His Pro Asp Lys Asn Xaa Xaa Xaa Xaa Ala Xaa Glu Xaa
                20                  25                  30

Lys Phe Xaa Glu Xaa Xaa Xaa Ala Tyr Xaa Xaa Leu Ser Asp Pro Xaa
                35                  40                  45

Xaa Xaa Lys Arg Xaa Xaa Tyr Asp
        50                  55

(2) INFORMATION FOR SEQ ID NO:29:

(i) SEQUENCE CHARACTERISTICS:
           (A) LENGTH: 5 amino acids
           (B) TYPE: amino acid
           (D) TOPOLOGY: linear (ii) MOLECULE TYPE: peptide (xi) SEQUENCE DESCRIPTION: SEQ ID NO:29:

Lys Ala Lys Ala Lys
1               5

(2) INFORMATION FOR SEQ ID NO:30:

(i) SEQUENCE CHARACTERISTICS:

(A) LENGTH: 5 amino acids
            (B) TYPE: amino acid
            (D) TOPOLOGY: linear (ii) MOLECULE TYPE: peptide (xi) SEQUENCE DESCRIPTION: SEQ ID NO:30:

Lys Ala His Ala Lys
1               5

(2) INFORMATION FOR SEQ ID NO:31:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (ix) FEATURE:
            (A) NAME/KEY: any amino acid
            (B) LOCATION: 5

(xi) SEQUENCE DESCRIPTION: SEQ ID NO:31:

Lys Ala Lys Ala Xaa
1               5

(2) INFORMATION FOR SEQ ID NO:32:

(i) SEQUENCE CHARACTERISTICS:
            (A) LENGTH: 16 amino acids
            (B) TYPE: amino acid
            (D) TOPOLOGY: linear (ii) MOLECULE TYPE: peptide (xi) SEQUENCE DESCRIPTION: SEQ ID NO:32:

Ala Lys Ala Lys Ala Glu Ala Glu Ala Lys Ala Lys Ala Glu Ala Glu
1               5                  10                  15

(2) INFORMATION FOR SEQ ID NO:33:

(i) SEQUENCE CHARACTERISTICS:
            (A) LENGTH: 16 amino acids
            (B) TYPE: amino acid
            (D) TOPOLOGY: linear (ii) MOLECULE TYPE: peptide (xi) SEQUENCE DESCRIPTION: SEQ ID NO:33:

Ala Lys Ala Glu Ala Lys Ala Glu Ala Lys Ala Glu Ala Lys Ala Glu
1               5                  10                  15

(2) INFORMATION FOR SEQ ID NO:34:

(i) SEQUENCE CHARACTERISTICS:
            (A) LENGTH: 16 amino acids
            (B) TYPE: amino acid
            (D) TOPOLOGY: linear (ii) MOLECULE TYPE: peptide (xi) SEQUENCE DESCRIPTION: SEQ ID NO:34:

Glu Ala Lys Ala Glu Ala Lys Ala Glu Ala Lys Ala Glu Ala Lys Ala
1               5                  10                  15

(2) INFORMATION FOR SEQ ID NO:35:

(i) SEQUENCE CHARACTERISTICS:
            (A) LENGTH: 16 amino acids

```
        (B) TYPE: amino acid
        (D) TOPOLOGY: linear (ii) MOLECULE TYPE: peptide (xi) SEQUENCE DESCRIPTION: SEQ ID NO:35:

Lys Ala Glu Ala Lys Ala Glu Ala Lys Ala Glu Ala Lys Ala Glu Ala
1               5                  10                  15

(2) INFORMATION FOR SEQ ID NO:36:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:36:

Ala Glu Ala Lys Ala Glu Ala Lys Ala Glu Ala Lys Ala Glu Ala Lys
1               5                  10                  15

(2) INFORMATION FOR SEQ ID NO:37:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:37:

Ala Asp Ala Asp Ala Arg Ala Arg Ala Asp Ala Asp Ala Arg Ala Arg
1               5                  10                  15

(2) INFORMATION FOR SEQ ID NO:38:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:38:

Ala Arg Ala Asp Ala Arg Ala Asp Ala Arg Ala Asp Ala Arg Ala Asp
1               5                  10                  15

(2) INFORMATION FOR SEQ ID NO:39:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:39:

Asp Ala Arg Ala Asp Ala Arg Ala Asp Ala Arg Ala Asp Ala Arg Ala
1               5                  10                  15

(2) INFORMATION FOR SEQ ID NO:40:

(i) SEQUENCE CHARACTERISTICS:
        (A) LENGTH: 16 amino acids
        (B) TYPE: amino acid
        (D) TOPOLOGY: linear (ii) MOLECULE TYPE: peptide
```

(xi) SEQUENCE DESCRIPTION: SEQ ID NO:40:

Arg Ala Asp Ala Arg Ala Asp Ala Arg Ala Asp Ala Arg Ala Asp Ala
1               5                   10                  15

(2) INFORMATION FOR SEQ ID NO:41:

(i) SEQUENCE CHARACTERISTICS:
        (A) LENGTH: 16 amino acids
        (B) TYPE: amino acid
        (C) TOPOLOGY: linear (xi) SEQUENCE DESCRIPTION: SEQ ID NO:41:

Ala Asp Ala Arg Ala Asp Ala Arg Ala Asp Ala Arg Ala Asp Ala Arg
1               5                   10                  15

(2) INFORMATION FOR SEQ ID NO:42:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:42:

Ala Arg Ala Asp Ala Lys Ala Glu Ala Arg Ala Asp Ala Lys Ala Glu
1               5                   10                  15

(2) INFORMATION FOR SEQ ID NO:43:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:43:

Ala Lys Ala Glu Ala Arg Ala Asp Ala Lys Ala Glu Ala Arg Ala Asp
1               5                   10                  15

(2) INFORMATION FOR SEQ ID NO:44:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:44:

Ala Arg Ala Lys Ala Asp Ala Glu Ala Arg Ala Lys Ala Asp Ala Glu
1               5                   10                  15

(2) INFORMATION FOR SEQ ID NO:45:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:45:

Ala Lys Ala Arg Ala Glu Ala Asp Ala Lys Ala Arg Ala Asp Ala Glu
1               5                   10                  15

(2) INFORMATION FOR SEQ ID NO:46:

(i) SEQUENCE CHARACTERISTICS:
    (A) LENGTH: 16 amino acids
    (B) TYPE: amino acid
    (D) TOPOLOGY: linear (ii) MOLECULE TYPE: peptide (xi) SEQUENCE DESCRIPTION: SEQ ID NO:46:

Ala Gln Ala Gln Ala Gln Ala Gln Ala Gln Ala Gln Ala Gln Ala Gln
1               5                  10                  15

(2) INFORMATION FOR SEQ ID NO:47:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:47:

Val Gln Val Gln Val Gln Val Gln Val Gln Val Gln Val Gln Val Gln
1               5                  10                  15

(2) INFORMATION FOR SEQ ID NO:48:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:48:

Tyr Gln Tyr Gln Tyr Gln Tyr Gln Tyr Gln Tyr Gln Tyr Gln Tyr Gln
1               5                  10                  15

(2) INFORMATION FOR SEQ ID NO:49:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:49:

His Gln His Gln His Gln His Gln His Gln His Gln His Gln His Gln
1               5                  10                  15

(2) INFORMATION FOR SEQ ID NO:50:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:50:

Ala Asn Ala Asn Ala Asn Ala Asn Ala Asn Ala Asn Ala Asn Ala Asn
1               5                  10                  15

(2) INFORMATION FOR SEQ ID NO:51:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:51:

Val Asn Val Asn Val Asn Val Asn Val Asn Val Asn Val Asn Val Asn
1               5                   10                  15

(2) INFORMATION FOR SEQ ID NO:52:

(i) SEQUENCE CHARACTERISTICS:
            (A) LENGTH: 16 amino acids
            (B) TYPE: amino acid
            (D) TOPOLOGY: linear (ii) MOLECULE TYPE: peptide (xi) SEQUENCE DESCRIPTION: SEQ ID NO:52:

Tyr Asn Tyr Asn Tyr Asn Tyr Asn Tyr Asn Tyr Asn Tyr Asn Tyr Asn
1               5                   10                  15

(2) INFORMATION FOR SEQ ID NO:53:

(i) SEQUENCE CHARACTERISTICS:
            (A) LENGTH: 16 amino acids
            (B) TYPE: amino acid
            (D) TOPOLOGY: linear (ii) MOLECULE TYPE: peptide (xi) SEQUENCE DESCRIPTION: SEQ ID NO:53:

His Asn His Asn His Asn His Asn His Asn His Asn His Asn His Asn
1               5                   10                  15

(2) INFORMATION FOR SEQ ID NO:54:

(i) SEQUENCE CHARACTERISTICS:
            (A) LENGTH: 16 amino acids
            (B) TYPE: amino acid
            (D) TOPOLOGY: linear (ii) MOLECULE TYPE: peptide (xi) SEQUENCE DESCRIPTION: SEQ ID NO:54:

Ala Asn Ala Gln Ala Asn Ala Gln Ala Asn Ala Gln Ala Asn Ala Gln
1               5                   10                  15

(2) INFORMATION FOR SEQ ID NO:55:

(i) SEQUENCE CHARACTERISTICS:
            (A) LENGTH: 16 amino acids
            (B) TYPE: amino acid
            (D) TOPOLOGY: linear (ii) MOLECULE TYPE: peptide (xi) SEQUENCE DESCRIPTION: SEQ ID NO:55:

Ala Gln Ala Asn Ala Gln Ala Asn Ala Gln Ala Asn Ala Gln Ala Asn
1               5                   10                  15

(2) INFORMATION FOR SEQ ID NO:56:

(i) SEQUENCE CHARACTERISTICS:
            (A) LENGTH: 16 amino acids
            (B) TYPE: amino acid
            (D) TOPOLOGY: linear (ii) MOLECULE TYPE: peptide (xi) SEQUENCE DESCRIPTION: SEQ ID NO:56:

```
Val Asn Val Gln Val Asn Val Gln Val Asn Val Gln Val Asn Val Gln
1               5                   10                  15
```

(2) INFORMATION FOR SEQ ID NO:57:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:57:

```
Val Gln Val Asn Val Gln Val Asn Val Gln Val Asn Val Gln Val Asn
1               5                   10                  15
```

(2) INFORMATION FOR SEQ ID NO:58:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:58:

```
Tyr Asn Tyr Gln Tyr Asn Tyr Gln Tyr Asn Tyr Gln Tyr Asn Tyr Gln
1               5                   10                  15
```

(2) INFORMATION FOR SEQ ID NO:59:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:59:

```
Tyr Gln Tyr Asn Tyr Gln Tyr Asn Tyr Gln Tyr Asn Tyr Gln Tyr Asn
1               5                   10                  15
```

(2) INFORMATION FOR SEQ ID NO:60:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:60:

```
His Asn His Gln His Asn His Gln His Asn His Gln His Asn His Gln
1               5                   10                  15
```

(2) INFORMATION FOR SEQ ID NO:61:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:61:

```
His Gln His Asn His Gln His Asn His Gln His Asn His Gln His Asn
1               5                   10                  15
```

(2) INFORMATION FOR SEQ ID NO:62:

```
    (i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:62:

Val Lys Val Gln Val Asp Val Lys Val Gln Val Asp Val Lys Val Gln
1               5                   10                  15

Val Asp (2) INFORMATION FOR SEQ ID NO:63:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:63:

Tyr Lys Tyr Gln Tyr Asp Tyr Lys Tyr Gln Tyr Asp Tyr Lys Tyr Gln
1               5                   10                  15

Tyr Asp (2) INFORMATION FOR SEQ ID NO:64:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (xi) SEQUENCE DESCRIPTION: SEQ ID NO:64:

His Lys His Gln His Asp His Lys His Gln His Asp His Lys His Gln
1               5                   10                  15

His Asp
```

We claim:

1. A method for in vitro cell culture comprising:
   a) adding a macroscopic membrane which in formed by self-assembly of amphiphilic peptides in an aqueous solution containing monovalent metal cations, wherein the peptides are 12 or more amino acids in length, have alternating hydrophobic and hydrophilic amino acids, and are complementary and structurally compatible, to a call culture medium comprising cells, thereby forming a membrane/culture mixture;
   b) maintaining the mixture under conditions sufficient for cell growth.

2. The method of claim 1 wherein the peptides are homogeneous.

3. The method of claim 1 wherein the macroscopic membrane was formed by self-assembly of a peptide (residues 310 to 317 of SEQ ID NO:2) having the sequence (Ala-Glu-Ala-Glu-Ala-Lys-Ala-Lys)$_n$, where n is greater than or equal to 2.

4. The method of claim 1 wherein the macroscopic membrane was formed by a peptide (residues 1 to 8 of SEQ ID NO:40) having the sequence (Arg-Ala-Asp-Ala-Arg-Ala-Asp-Ala)$_n$, where n is greater than or equal to 2.

* * * * *